(12) United States Patent
Tran

(10) Patent No.: US 12,277,997 B1
(45) Date of Patent: Apr. 15, 2025

(54) RAPID, COMPREHENSIVE AND SENSITIVE METHOD FOR NEOANTIGEN SCREENING FROM RECURRENT CANCER MUTATIONS

(71) Applicant: Le Son Tran, Ho Chi Minh (VN)

(72) Inventor: Le Son Tran, Ho Chi Minh (VN)

(73) Assignee: NEXCALIBUR THERAPEUTICS, CORP., Lewes, DE (US)

( * ) Notice: Subject to any disclaimer, the term of this patent is extended or adjusted under 35 U.S.C. 154(b) by 0 days.

(21) Appl. No.: 18/492,794

(22) Filed: Oct. 24, 2023

(51) Int. Cl.
| | |
|---|---|
| *G16B 35/10* | (2019.01) |
| *C07K 14/00* | (2006.01) |
| *C12N 5/078* | (2010.01) |
| *C12N 15/86* | (2006.01) |
| *G16B 20/20* | (2019.01) |
| *G16B 35/20* | (2019.01) |
| *G16B 50/30* | (2019.01) |

(52) U.S. Cl.
CPC ............ *G16B 35/10* (2019.02); *C07K 14/001* (2013.01); *C12N 5/0634* (2013.01); *C12N 15/86* (2013.01); *G16B 20/20* (2019.02); *G16B 35/20* (2019.02); *G16B 50/30* (2019.02); *C12N 2740/15043* (2013.01)

(58) Field of Classification Search
CPC ........ G16B 35/10; G16B 20/20; G16B 35/20; G16B 50/30; C07K 14/001; C12N 5/0634; C12N 15/86; C12N 2740/15043
See application file for complete search history.

(56) References Cited

PUBLICATIONS

Borden ES. Cancer neoantigens: challenges and future directions for prediction, prioritization, an validation. Frontiers in Oncology 12: 1-22. (Year: 2022).*
Lo AA. Indication-specific tumor evolution and its impact on neoantigen targeting and biomarkers for individualized cancer immunotherapies. Journal for ImmunoTherapy of Cancer 9: e003001, 1-13. (Year: 2021).*
Kim S. Neopepsee: accurate genome-level prediction of neoantigens by harnessing sequence and amino acid immunogenicity information. Annals of Oncology 29: 1030-1036. (Year: 2018).*
Wirth TC. Neoantigen targeting—dawn of a new era in cancer immunotherapy? Frontiers in Immunotherapy 8(1848):1-16. (Year: 2017).*
Liang Z. The common antigens in colorectal cancer are predicted and validated to be presented or immunogenic. bioaRxiv 682617:1-47. (Year: 2019).*

\* cited by examiner

*Primary Examiner* — Olivia M. Wise
*Assistant Examiner* — Robert J. Kallal

(57) ABSTRACT

A rapid, comprehensive and sensitive method for neoantigen screening from recurrent cancer mutations comprising: (A) STEP 1: selecting recurrent cancer mutations dividing into three tiers based on ranking features; (B) STEP 2: Generating a library of artificial antigen presenting cells (aAPC) co-expressing HLA types (including a list of 13 most frequent HLA class I types covering 66% of Asian population or 67% of Vietnamese population, and a list of 04 most frequent HLA class II types covering 41% Asian population or 50% of Vietnamese population) and a co-stimulatory molecule; and (C) STEP 3: Using the library of aAPC at step (B) for rapid and comprehensive screening for selecting of immunogenic peptides (neoantigens) from the off-the-shelf peptides at step (A) activate T cells via immunological assays (ELISpot or intracellular staining flow cytometry).

7 Claims, 15 Drawing Sheets

RAPID, COMPREHENSIVE AND SENSITIVE METHOD FOR NEOANTIGEN SCREENING FROM RECURRENT CANCER MUTATIONS

FIELD OF THE INVENTION

The present invention relates to the field of molecular biology. Specifically, it provides a comprehensive and effective workflow for screening T-cell responses to cancer-specific neoantigens using artificial antigen-presenting cells. More specifically, the present invention relates to a method for screening neoantigens immunogenic performed.

BACKGROUND ART

Neoantigen is a type of tumor-specific antigen which is only expressed on tumor cells harboring somatic mutation. Many computational algorithms and machine-learning tools have been developed to identify mutations in sequence data and predict neoantigens. So far only few neoantigens could activate immunogenicity of T cell response from a list of predicted neoantigens therefore screening of potential neoantigen in clinical is crucial for neoantigen-based immunotherapy.

Immunological ELISpot assays are widely used to detect and quantify antigen-specific T cells in PBMCs from patients with cancer or chronic viral infections in clinical setting. However, the limited number of native antigen-presenting cells (APC) in patients' PBMCs and the time-consuming procedure to induce maturation of those APC are the two major disadvantages of current ELISpot assays. To increase the capacity and shorten the screening procedure, artificial APC (aAPC) generated from immortalized cell lines have been developed.

The human lymphoid hybrid T2 or HLA-transfected insect cells have been used as aAPC for neoantigen screening. However, they exhibit poor antigen presentation capacity and high signal background when activated in vitro (PMID: 11730845). Conversely, the human chronic myelogenous leukemia cell line K562 has emerged as a potential aAPC candidate for several reasons. First, K562 cells are lack of endogenous expression of HLA class I and class II molecules (PMID: 66956). Second, they have high transfection efficiency, facilitating the generation of HLA transfected K562 cells (PMID: 11730845). Third, they also express ICAM (CD54) and LFA-3 (CD58), thus providing needed for effective T cell-APC interactions (PMID: 17363542). Additionally, K562 cells secrete MCSF, IL-6, IL-8, TGF-β, and MIP-1α but do not secrete the γ-chain receptor cytokines IFNγ or IL-10 (PMID: 17363542). Engineered K562 cells are commonly employed in specific immunology investigations due to their absence of HLA-I and HLA-II expression. Nevertheless, they may not be the primary preference for neoantigen screening because they may not faithfully replicate the HLA profile of the patient's tumor cells, potentially impacting the relevance of the neoantigen screening outcomes. Therefore, we have generated an off-the shelf library of aAPC expressing the most prevalent HLA-I and HLA-II alleles in Asian populations and develop optimized screening procedures to achieve comprehensive and fast screening for immunogenic neopeptide candidates for cancer patients.

ELISpot assays are widely used to detect and quantify single antigen-specific T cells in PBMCs from cancer patients. However, the use of aAPC cells for screening neoantigens has not been widely used due to the lack of a comprehensive library of HLA-matched antigen-presenting cells (APC) that can cover all HLA types in particular populations such as Asian populations. Thus, the construction of aAPC library cells is required to increase the coverage of HLA-I and HLA-II alleles and reduce the time of obtaining many activated antigen presenting cells is essential to tackle this challenge.

According to Patent No. US2011262467A1, the invention refers to an isolated artificial antigen presenting cell (aAPC), said aAPC comprising a K562 cell transduced using a lentiviral vector (LV), wherein said LV comprises a nucleic acid encoding at least one immune stimulatory ligand (stimulatory ligand is a polypeptide selected from the group consisting of a major histocompatibility complex Class I (MHC class I) molecule loaded with an antigen, an anti-CD3 antibody, an anti-CD28 antibody, and an anti-CD2 antibody) and at least one co-stimulatory molecules (co-stimulatory molecules is at least one co-stimulatory molecules selected from the group consisting of CD7, B7-1 (CD80), B7-2 (CD86), PD-L1, PD-L2, 4-1BBL, OX40L, ICOS-L, ICAM, CD30L, CD40, CD70, CD83, HLA-G, MICA, MICB, HVEM, lymphotoxin beta receptor, ILT3, ILT4, 3/TR6, and a ligand that specifically binds with B7-H3). aAPC expresses said stimulatory ligand and said co-stimulatory molecules and can stimulate and expand neoantigen-reactive T cells, thereby enhancing the sensitivity of neoantigen detection.

According to Patent No. US20210057043A1, the invention refers to A tumor neoantigen prediction platform and an application thereof in a neoantigen vaccine development system are provided. The present invention selects 55 HLA-A and HLA-B subtypes with a high proportion of the Chinese population from a common database, then establishes a method for constructing cell lines expressing associated HLA subtypes, builds a high-frequency HLA-binding polypeptide database for the Chinese population; subsequently, a tumor neoantigen prediction algorithm is optimized by a prediction platform including the HLA-binding polypeptide database, thereby significantly improving the tumor neoantigen prediction accuracy. The 55 HLA subtypes comprise 24 HLA-A subtypes and 31 HLA-B subtypes, numbered explicitly as follows: HLA-A*01:01, HLA-A*02:01, HLA-A*02:02, HLA-A*02:03, HLA-A*02:04, HLA-A*02:05, HLA-A*02:06, HLA-A*02:07, HLA-A*03:01, HLA-A*11:01, HLA-A*11:02, HLA-A*23:01, HLA-A*24:02, HLA-A*24:03, HLA-A*26:01, HLA-A*29:02, HLA-A*30:01, HLA-A*31:01, HLA-A*32:01, HLA-A*33:01, HLA-A*33:03, HLA-A*66:01, HLA-A*68:01, HLA-A*68:02, HLA-B*07:02, HLA-B*08:01, HLA-B*13:01, HLA-B*13:02, HLA-B*15:01, HLA-B*15:02, HLA-B*15:10, HLA-B*27:02, HLA-B*27:03, HLA-B*27:05, HLA-B*27:06, HLA-B*35:01, HLA-B*38:01, HLA-B*38:02, HLA-B*39:01, HLA-B*39:09, HLA-B*39:011, HLA-B*40:01, HLA-B*40:02, HLA-B*40:06, HLA-B*44:02, HLA-B*44:03, HLA-B*46:01, HLA-B*48:01, HLA-B*51:01, HLA-B*52:01, HLA-B*53:01, HLA-B*54:01, HLA-B*55:02, HLA-B*57:01, and HLA-B*58:01.

Kazushi Tanimoto, et al (PMID: 24176543) describe the human leukemia cell line K562 represents an attractive platform for creating artificial antigen-presenting cells (aAPC). Transduced K562 with HLA-A*0201 in combination with co-stimulatory molecules. Full abrogation of the suppressive activity of K562 on MLR, SEB, and OKT3 stimulation was only achieved by brief fixation with 0.1% formaldehyde.

Maria Parkhurst, et al (PMID: 27827318) describe some tumor-infiltrating lymphocytes (TIL) recognize somatic mutations. Mutations expressed by tumors were identified using whole-exome and RNA sequencing. Tandem minigene (TMG) constructs encoding 12-24 mutated gene products were synthesized, each encoding the mutated amino acid flanked by 12 amino acids of the normal protein sequence. Methods include Tumor biopsies and white blood cell products taken from people with stage IV melanoma; Whole-exome sequencing and RNA sequencing; Isolation of TIL populations; Generation of autologous dendritic cells; Construction of tandem minigene constructs and in vitro transcription of TMG RNA; Initial screening of TILs for recognition of mutated antigens.

The above inventions meet the specific purposes and requirements of a technical solution. However, the above inventions only refer to step-by-step preparation using K562 cell transduced HLA and a co-stimulatory molecule as artificial antigen-presenting cells; selects 55 HLA-A and HLA-B subtypes with a high proportion of the Chinese population from a common database, predicting neoantigen of the tumor by a prediction platform that includes a database of associated polypeptides, associated with HLA, and identification of mutated T-cell antigens by screening the Tandem minigenes library. Construction of tandem minigene (TMG) constructs encoding 12-24 mutant gene products for screening and recognition of mutant antigens. However, the above inventions does not disclose the following issues:

(1) Classifying the set of selected mutations into three different tiers based on ranking features including: (a) the mutations concurrently detected in early and late-stage tumors, (b) the mutations with high frequencies, and (c) the mutations predicted to have strong binding ability to common HLA types in the Vietnamese population;

(2) Based on the results of classification of said selected mutations, perform designing and synthesizing a collection includes a first collection of 67 off-the-shelf peptides dividing into three tiers and a second collection of tandem minigene (TMG) constructs carrying selected mutations from the first collection of 67 off-the-shelf peptides dividing into three tiers reflecting their high recurrence rates, functional importance in tumorigenesis and high predicted immunogenicity;

(3) Generating a library of artificial antigen presenting cells (aAPC) co-expressing HLA types and the co-stimulatory molecule; wherein HLA type data collected from public database and ranking HLA types based on their frequencies in different Asian populations including a list of 13 most frequent HLA class I types covering 66% of Asian population or 67% of Vietnamese population, and a list of 04 most frequent HLA class II types covering 41% Asian population or 50% of Vietnamese population is obtained;

(4) Proposed a method of rapid and comprehensive screening for selecting of immunogenic peptides (neoantigens) from the off-the-shelf peptides or TMGs activate T cells by using the library of aAPC via immunological assays (ELISpot or intracellular staining flow cytometry);

(5) The above method of rapid and comprehensive screening by using the library of aAPC co-expressing HLA types and CD80 molecule for screening immunogenic peptides with weak TCR and peptide-HLA binding affinity;

(6) The above method of rapid and sensitive screening by using the library of aAPC for screening and selecting immunogenic peptides (neoantigens) from the off-the-shelf peptides that activate T cells within 9 days;

(7) The above method of rapid and comprehensive screening by using the library of aAPC for screening and selecting immunogenic peptides (neoantigens) from TMGs activate T cells within 11 days; and (8) The above method of rapid and comprehensive screening by using the library of aAPC for screening immunogenic peptides from the off-the-shelf peptides or TMGs that can activate both CD4+ T cells and CD8+ T cells or exclusively activate CD8+ T cells.

The invention provides solutions to achieve the above objectives.

SUMMARY OF THE INVENTION

Accordingly, an objective of the present invention is to provide a rapid, comprehensive and sensitive method for neoantigen screening from recurrent cancer mutations comprising steps performed in the following specific order:

(A) STEP 1: selecting recurrent cancer mutations by performing steps (i) to (iv):

(i) Collecting cancer mutation data from TCGA database: two projects (TCGA-COAD and TCGA-LUAD) are downloaded, then Data are pre-processed by VarScan to obtain a set of selected mutations including single nucleotide variations (SNVs), and insertions/deletions variants (Indels);

(ii) Classifying the set of selected mutations into three different tiers based on ranking features including: (a) the mutations concurrently detected in early and late-stage tumors, (b) the mutations with high frequencies, and (c) the mutations predicted to have strong binding ability to common HLA types in the Vietnamese population;

wherein three tiers including a first tier, a second tier, and a third tier;

wherein the first tier includes mutated peptides having all three rank features including (a), (b) and (c);

wherein the second tier includes mutated peptides having two rank features (b) and (c);

wherein the third tier includes mutated peptides having two rank features (a) and (b); and (iii) Evaluating the recurrence of selected mutations from the three tiers in cohorts of colorectal cancer (CRC) (n=50) and lung cancer patients (n=50);

(iv) Designing and synthesizing a collection includes: a first collection, and a second collection; wherein the first collection of 67 off-the-shelf peptides (referred to as the off-the-shelf peptides) carrying SNVs and Indels (listed in Table 1 below) including 42 SNVs and 25 Indels; wherein the first collection of 67 off-the-shelf peptides dividing into three tiers including the first tier consist of 12 SNVs and 2 indels, the second tier consist of 11 SNVs and 6 indels, and the third tier consist of 19 SNVs and 17 indels;

the second collection of tandem minigene (TMG) constructs (referred to as the TMGs) carrying selected mutations from the first collection of 67 off-the-shelf peptides dividing into three tiers; wherein each TMG containing ten minigenes constructs encoding polypeptides carrying mutated amino acids and 12 amino acids flanked at C and N-terminal;

(B) STEP 2: Generation a library of artificial antigen presenting cells (aAPC) co-expressing HLA types (including HLA-I and HLA-II alleles highly detected in Asian populations) and a co-stimulatory molecule (referred to as the library of aAPC) by performing the steps:

(i') collecting HLA type data from public database and ranking HLA types based on their frequencies in different Asian populations; As a result, a list of 13 most frequent HLA class I types covering 66% of Asian population or 67% of Vietnamese population, and a list of 04 most frequent HLA class II types covering 41% Asian population or 50% of Vietnamese population is obtained; and (ii') generating the library of aAPC including a library of aAPC by genetically engineering K562 cells to the co-express selected HLA class I types at step (i') and the co-stimulatory molecule; and a library of aAPC by genetically engineering K562 cells to co-express selected HLA class II types at step (i') and the co-stimulatory molecule;

(C) STEP 3: using the library of aAPC at step (B) for rapid and comprehensive screening for selecting of immunogenic peptides (neoantigens) from the off-the-shelf peptides at step (A) or TMGs at step (A) activate T cells via immunological assays (ELISpot or intracellular staining flow cytometry).

Another objective of the present invention is to provide a method generating the library of aAPC by genetically engineering K562 cells to co-express HLA class I types and the co-stimulatory molecule; wherein the co-stimulatory molecule is CD80 molecule.

Yet another objective of the present invention is to provide a method generating the library of aAPC by genetically engineering K562 cells to co-express HLA class II types and the co-stimulatory molecule; wherein the co-stimulatory molecule is CD80 molecule.

In view of the foregoing, another objective of the present invention is to provide a method of rapid and comprehensive screening by using the library of aAPC for screening and selecting immunogenic peptides (neoantigens) from the off-the-shelf peptides activate T cells within 9 days, comprising the following steps:

(A') At day 1: generating a peptide-pulsed aAPC;
  (a1) T cells isolated from PBMCs of healthy donor carrying appropriated HLA class I or HLA class II type are cultured in AIM-V media supplemented with 10% FBS, and 10 ng/ml of IL-21; and T cells are enriched by CD3 marker;
  (b1) Corresponding K562 aAPC cells expressing HLA class I or HLA class II are cultured in RPMI1640 media supplemented with 10% FBS, and 1% PS;
    wherein said culture media is exchanged to OptiMEM media without FBS to enhance the exogenous peptide uptake;
    wherein 25 µM of each peptide is pulsed with aAPC cells for 3 hours; in which each peptide consists of 25 amino acids covering mutations classified into three tiers of the first collection of off-the-shelf peptides;
  (c1) OptiMEM media is removed, and cells are washed two times with PBS; results obtained the peptide-pulsed aAPC;

(B') From day 1 to day 3: generating an antigen-specific T cells comprising the following steps:
  Fixing the peptide-pulsed aAPC with 0.1% formaldehyde for ten minutes at room temperature (RT);
  Washing one time with PBS and one time with culture media to remove formaldehyde; and
  Co-culture with T cells in T cell media supplemented IL-7 (10 ng/ml), IL-21 (10 ng/ml), IL-15 (10 ng/mL) at the ratio of 2:1 (T cells: fixed aAPC cells) for 3 days;
    wherein T cells isolated from PBMCs of healthy donor carrying appropriated HLA class I or HLA class II type are cultured in AIM-V media supplemented with 10% FBS, and 10 ng/mL of IL-21; and T cells are enriched by CD3 marker;

(C') From day 3 to day 6: The antigen-specific T cells were restimulated via the peptide-pulsed aAPC at step (B') in T cell media without interleukin stimulation overnight; and then co-culture with T cells in T cell media supplemented IL-7 (10 ng/ml), IL-21 (10 ng/ml), IL-15 (10 ng/ml) for 3 days;

(D') At day 7: Restimulate antigen-specific T cells with peptide-pulsed aAPC and coculture in media without cytokines;

(E') At day 8: $10^5$ T cells are counted and seeded into ELISpot plate for interferon-γ quantification; and (F') At day 9: Quantification of interferon-γ newly isolated peripheral blood mononuclear cells (PBMCs) by ELISpot assay, resulting obtained to the immunogenic peptides (neoantigens);
  wherein based on spots from mutant (MT) peptides and wild type (WT) peptides are measured by ELISpot reader, peptides with MT/WT fold change greater than or equal to 2 (≥2) are defined as immunogenic peptides.

Finally, the purpose of the present invention is to provide a method of rapid and comprehensive screening by using the library of aAPC for screening and selecting immunogenic peptides (neoantigens) from TMGs activate T cells within 11 days, comprising the following steps:

(A") At day 1: generating a TMG mRNA-transfected aAPC;
  (a2) T cells isolated from PBMCs of healthy donor carrying appropriated HLA class I or HLA class II type are cultured in AIM-V media supplemented with 10% FBS, and 10 ng/ml of IL-21; and T cells are enriched by CD3 marker;
  (b2) Corresponding K562 aAPC cells expressing HLA class I or HLA class II are cultured in RPMI1640 media supplemented with 10% FBS, and 1% PS;
  (c2) TMG mRNAs are invitro synthesized and transfected into K562 aAPC cells by using Lipofectamine MessengerMAX; and then cultured for overnight; results obtained the TMG mRNA-transfected aAPC;

(B") From day 2 to day 5: generating an antigen-specific T cells comprising the following steps:
  Fixing the TMG mRNA-transfected aAPC with 0.1% formaldehyde for ten minutes at room temperature (RT);
  Washing one time with PBS and one time with culture media to remove formaldehyde; and then co-culture with T cells in T cell media supplemented IL-7 (10 ng/ml), IL-21 (10 ng/mL), IL-15 (10 ng/ml) at the ratio of 2:1 (T cells: fixed aAPC cells) for 3 days;
    wherein T cells isolated from PBMCs of healthy donor carrying appropriated HLA class I or HLA class II type are cultured in AIM-V media supplemented with 10% FBS, and 10 ng/ml of IL-21; and T cells are enriched by CD3 marker;

(C") From day 5 to day 8: The antigen-specific T cells were restimulated via the TMG mRNA-transfected aAPC at step (B') in T cell media without interleukin stimulation overnight; and then co-culture with T cells in T cell media supplemented IL-7 (10 ng/ml), IL-21 (10 ng/ml), IL-15 (10 ng/ml) for 3 days;

(D") At day 9: Restimulate antigen-specific T cells with TMG mRNA-transfected aAPC and coculture in media without cytokines;

(E") At day 10: $10^5$ T cells are counted and seeded into ELISpot plate for interferon-γ quantification; and (F") At day 11: Quantification of interferon-γ newly isolated peripheral blood mononuclear cells (PBMCs) by ELISpot assay, resulting obtained to the immunogenic peptides (neoantigens);

wherein based on spots from mutant (MT) TMGs and corresponding wild type (WT) TMGs are measured by ELISpot reader, peptides with MT/WT fold change greater than or equal to 2 (≥2) are defined as immunogenic peptides.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWINGS

The accompanying drawings, which are incorporated in and form a part of this specification, illustrate embodiments of the invention and, together with the description, explain the principles of the invention.

DETAILED DESCRIPTION OF THE INVENTION

Figure 1:
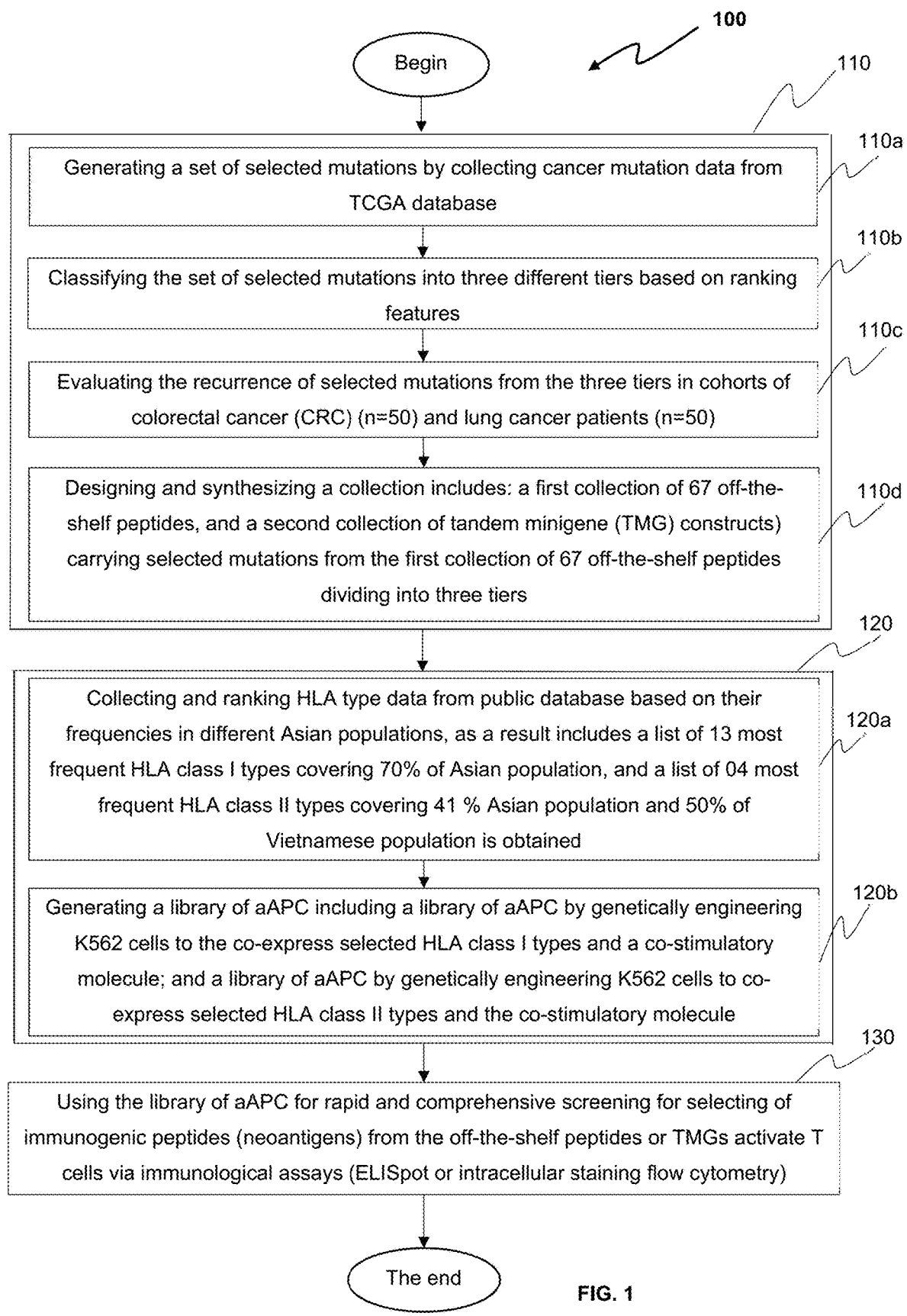
FIG. 1 is a flowchart illustrated a flowchart of a rapid, comprehensive and sensitive method for screening neoantigens derived from recurrent cancer mutations based on the above principle in accordance with an exemplary embodiment of the present invention.

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications, and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

Within the scope of the present invention, the term "HLA" meaning is human leukocyte antigens are genes in major histocompatibility complexes (MHC) that help code for proteins that differentiate between self and non-self. They play a significant role in disease and immune defense.

One embodiment of the invention is now described with reference to FIG. 1. illustrated a rapid, comprehensive and sensitive method for neoantigen screening from recurrent cancer mutations 100 ("method 100") based on the above principle in accordance with an exemplary embodiment of the present invention. In particular, method 100 includes the following three steps: step 110, step 120, and step 130.

Begin at step 110, selecting recurrent cancer mutations by performing from step 110a to step 110d. At step 110a, collecting cancer mutation data from TCGA database. Two projects (TCGA-COAD and TCGA-LUAD) are downloaded, then data are pre-processed by VarScan to obtain a set of selected mutations including single nucleotide variations (SNVs), and insertions/deletions variants (Indels).

At step 110b, classifying the set of selected mutations at step 110a into three different tiers based on ranking features including: (a) the mutations concurrently detected in early and late-stage tumors, (b) the mutations with high frequencies, and (c) the mutations predicted to have strong binding ability to common HLA types in the Vietnamese population.

According to the embodiment of the invention, said three tiers including a first tier, a second tier, and a third tier. The first tier includes mutated peptides having all three rank features including (a), (b) and (c). The second tier includes mutated peptides having two rank features (b) and (c). The third tier includes mutated peptides having two rank features (a) and (b).

At step 110c, evaluating the recurrence of selected mutations from the three tiers in cohorts of colorectal cancer (CRC) (n=50) and lung cancer patients (n=50).

At step 110d, designing and synthesizing a collection includes: a first collection, and a second collection. According to the embodiment of the invention, the first collection of 67 off-the-shelf peptides (referred to as the off-the-shelf peptides) carrying SNVs and Indels including 42 SNVs and 25 Indels, that all listed in Table 1 below.

TABLE 1

The first collection of 67 off-shelf peptides classified into three tiers

| No. | Tier | Mutation position |
|---|---|---|
| 1 | 1 | KRAS_p.G13D |
| 2 | 1 | KRAS_p.G12V |
| 3 | 1 | KRAS_p.G12A |
| 4 | 1 | KRAS_p.G12D |
| 5 | 1 | KRAS_p.G12C |
| 6 | 1 | CDX2_p.V306X |
| 7 | 1 | RNF43_p.G659X |
| 8 | 1 | TP53_p.R282W |
| 9 | 1 | TP53_p.R273H |
| 10 | 1 | TP53_p.R248Q |
| 11 | 1 | TP53_p.R175H |
| 12 | 1 | GNAS_p.R201H |
| 13 | 1 | PIK3CA_p.E545K |
| 14 | 1 | BRAF_p.V640E |
| 15 | 2 | TCF7L2_p.R471C |
| 16 | 2 | ATM_p.A2301X |
| 17 | 2 | POU2AF1_p.A226V |
| 18 | 2 | KRAS_p.G12S |
| 19 | 2 | CHD4_p.K73X |
| 20 | 2 | TP53_p.E286K |
| 21 | 2 | TP53_p.Y220C |
| 22 | 2 | TP53_p.C176F |
| 23 | 2 | TP53_p.A159P |
| 24 | 2 | TP53_p.V157F |
| 25 | 2 | CIC_p.T1740M |
| 26 | 2 | ELK4_p.S359X |
| 27 | 2 | ARID1A_p.K1071X |
| 28 | 2 | BARD1_p.K171X |
| 29 | 2 | PIK3CA_p.V344G |
| 30 | 2 | PIK3CA_p.E542K |
| 31 | 2 | AKAP9_p.SE1650-1651SX |
| 32 | 3 | TCF7L2_p.H198X |
| 33 | 3 | ATM_p.V60X |
| 34 | 3 | BCL9L_p.Q452X |
| 35 | 3 | NCOR2_p.P975X |
| 36 | 3 | KRAS_p.A146T |
| 37 | 3 | BRCA2_p.Q1782X |
| 38 | 3 | CDK12_p.R663C |
| 39 | 3 | TP53_p.R273C |
| 40 | 3 | SMAD4_p.G30X |
| 41 | 3 | SMAD4_p.R361H |
| 42 | 3 | MTOR_p.S2215F |
| 43 | 3 | ATP1A1_p.G98X |
| 44 | 3 | ARID1A_p.S764SX |
| 45 | 3 | ARID1A_p.G1848X |
| 46 | 3 | ASXL1_p.G643X |
| 47 | 3 | GNAS_p.R201C |
| 48 | 3 | ERG_p.-446-447X |
| 49 | 3 | AMER1_p.F173X |
| 50 | 3 | DCTN1_p.R1173H |
| 51 | 3 | PIK3CA_p.R88Q |
| 52 | 3 | PIK3CA_p.R357Q |
| 53 | 3 | PIK3CA_p.E545A |
| 54 | 3 | PIK3CA_p.E970K |
| 55 | 3 | FAT4_p.L3V |
| 56 | 3 | FBXW7_p.S582L |
| 57 | 3 | FBXW7_p.R465H |
| 58 | 3 | PDGFRA_p.R151H |
| 59 | 3 | APC_p.M1413X |
| 60 | 3 | APC_p.KR1462-1463X |
| 61 | 3 | IL7R_p.K119X |
| 62 | 3 | IL6ST_p.K529X |
| 63 | 3 | BRAF_p.D634N |
| 64 | 3 | BRAF_p.G509V |
| 65 | 3 | EGFR_p.L858R |
| 66 | 3 | AKAP9_p.K37X |
| 67 | 3 | UBR5_p.R1331C |

Based on Table 1, the first collection of 67 off-the-shelf peptides dividing into three tiers including the first tier consist of 12 SNVs and 2 indels, the second tier consist of 11 SNVs and 6 indels, and the third tier consist of 19 SNVs and 17 indels.

According to the embodiment of the invention, the second collection of tandem minigene (TMG) constructs (referred to as the TMGs) carrying selected mutations from the first collection of 67 off-the-shelf peptides dividing into three tiers; wherein each TMG containing ten minigenes constructs encoding polypeptides carrying mutated amino acids and 12 amino acids flanked at C and N-terminal.

Remain in FIG. 1, at step 120, generating a library of artificial antigen presenting cells (aAPC) co-expressing HLA types and a co-stimulatory molecule (referred to as the library of aAPC), wherein HLA types includes HLA-I and HLA-II alleles highly detected in Asian populations.

According to the embodiment of the invention, generating the library of aAPC by performing from step 120a to step 120b. Within the scope of the present invention, the term "aAPC" meaning is artificial antigen-presenting cells are modular, universal particles that target T cells to improve T cell therapies and study basic T cell immune responses. Our teams have developed aAPC platforms and applications for antigen-specific T-cell therapy. Using basic engineering approaches, they are modifiable to enhance cell and organ targeting and disease treatment. aAPCs can enhance, or even replace, endogenous cells during each step of generating an antigen-specific T cell response—from antigen presentation and T cell activation to T cell maintenance.

At step 120a, collecting HLA type data from public database and ranking HLA types based on their frequencies in different Asian populations. As a result includes a list of 13 most frequent HLA class I types covering 66% of Asian population or 67% of Vietnamese population, and a list of 04 most frequent HLA class II types covering 41% Asian population or 50% of Vietnamese population is obtained.

According to the preferred embodiment of the present invention, the list of 13 alleles HLA class I types covering 66% of Asian population or 67% of Vietnamese population, and the list of 04 most frequent HLA class II types covering 41% Asian population or 50% of Vietnamese population by performing as follows:

- access the Allele Frequency Net Database, and choose the option "HLA frequency search";
- focusing on 7 Asian populations including China, Indonesia, Japan, Malaysia, Viet Nam, South Korea, and Thailand on the page shows the filter for target HLA searching create to the list of HLA types is sorted from highest to smallest frequency (referenced by Table 2 to Table 6 below); wherein the allele frequency of each HLA type in every population is cumulated up to 100%;
- based on Table 2 to Table 4, selecting 13 HLA-I types with the highest frequencies for each locus of HLA-I comprising three main group alleles: HLA-A, HLA-B, and HLA-C; as a result the list of 13 alleles HLA class I types covering 66% of Asian population or 67% of Vietnamese population; and
- based on Table 5 to Table 6, selecting 04 HLA-II types with the highest frequencies for each locus of HLA-II comprising two main group alleles: HLA-DRB1, and HLA-DQB1; as a result the list of 04 alleles HLA class II types overing 41% Asian population or 50% of Vietnamese population.

TABLE 2

List of 82 alleles of the group HLA-A alleles and frequencies in 7 Asian population

| No. | HLA-A | Frequency | Accumulative |
|---|---|---|---|
| 1 | A*2402 | 0.347 | 0.347 |
| 2 | A*0201 | 0.115 | 0.462 |
| 3 | A*1101 | 0.101 | 0.563 |
| 4 | A*3303 | 0.085 | 0.648 |
| 5 | A*0206 | 0.078 | 0.726 |
| 6 | A*3101 | 0.078 | 0.804 |
| 7 | A*2601 | 0.069 | 0.873 |
| 8 | A*0207 | 0.032 | 0.905 |
| 9 | A*2603 | 0.021 | 0.926 |
| 10 | A*2602 | 0.016 | 0.942 |
| 11 | A*2407 | 0.009 | 0.951 |
| 12 | A*0101 | 0.006 | 0.957 |
| 13 | A*0301 | 0.005 | 0.962 |
| 14 | A*3301 | 0.004 | 0.966 |
| 15 | A*0203 | 0.004 | 0.970 |
| 16 | A*0210 | 0.004 | 0.974 |
| 17 | A*3001 | 0.004 | 0.978 |
| 18 | A*3401 | 0.003 | 0.981 |
| 19 | A*0202 | 0.002 | 0.983 |
| 20 | A*2410 | 0.001 | 0.984 |
| 21 | A*0302 | 0.001 | 0.985 |
| 22 | A*2901 | 0.001 | 0.986 |
| 23 | A*3004 | 0.001 | 0.987 |
| 24 | A*0218 | 0.001 | 0.988 |
| 25 | A*6801 | 0.001 | 0.989 |
| 26 | A*2605 | 0.001 | 0.990 |
| 27 | A*7401 | 0.0004 | 0.9894 |
| 28 | A*2408 | 0.0003 | 0.9897 |
| 29 | A*2301 | 0.0002 | 0.9899 |
| 30 | A*2403 | 0.0002 | 0.9901 |
| 31 | A*2488 | 0.0001 | 0.9902 |
| 32 | A*2404 | 0.0001 | 0.9903 |
| 33 | A*3312 | 0.0001 | 0.9904 |
| 34 | A*2426 | 0.0001 | 0.9905 |
| 35 | A*0228 | 0.0001 | 0.9906 |
| 36 | A*0253 | 0.0001 | 0.9907 |
| 37 | A*2606 | 0.0001 | 0.9908 |
| 38 | A*2464 | 0.0001 | 0.9909 |
| 39 | A*2425 | 0.0001 | 0.9910 |

TABLE 2-continued

List of 82 alleles of the group HLA-A alleles and frequencies in 7 Asian population

| No. | HLA-A | Frequency | Accumulative |
|---|---|---|---|
| 40 | A*2428 | 0.0001 | 0.9911 |
| 41 | A*0222 | 0.0001 | 0.9912 |
| 42 | A*0225 | 0.0001 | 0.9913 |
| 43 | A*1137 | 0.0001 | 0.9914 |
| 44 | A*2427 | 0.0001 | 0.9915 |
| 45 | A*0205 | 0.0001 | 0.9916 |
| 46 | A*2435 | 0.0001 | 0.9917 |
| 47 | A*1112 | 0.0001 | 0.9918 |
| 48 | A*1133 | 0.0001 | 0.9919 |
| 49 | A*0216 | 0.0001 | 0.9920 |
| 50 | A*0260 | 0.0001 | 0.9921 |
| 51 | A*0261 | 0.0001 | 0.9922 |
| 52 | A*1103 | 0.0001 | 0.9923 |
| 53 | A*1113 | 0.0001 | 0.9924 |
| 54 | A*6601 | 0.0001 | 0.9925 |
| 55 | A*3111 | 0.0001 | 0.9926 |
| 56 | A*2618 | 0.0001 | 0.9927 |
| 57 | A*1143 | 0.0001 | 0.9928 |
| 58 | A*1105 | 0.0001 | 0.9929 |
| 59 | A*0213 | 0.0001 | 0.9930 |
| 60 | A*2405 | 0.0001 | 0.9931 |
| 61 | A*3214 | 0.00002 | 0.99312 |
| 62 | A*2446 | 0.00002 | 0.99314 |
| 63 | A*2415 | 0.00002 | 0.99316 |
| 64 | A*2420 | 0.00002 | 0.99318 |
| 65 | A*2471 | 0.00002 | 0.99320 |
| 66 | A*0239 | 0.00002 | 0.99322 |
| 67 | A*0265 | 0.00002 | 0.99324 |
| 68 | A*0279 | 0.00002 | 0.99326 |
| 69 | A*0103 | 0.00002 | 0.99328 |
| 70 | A*0304 | 0.00002 | 0.99330 |
| 71 | A*0278 | 0.00002 | 0.99332 |
| 72 | A*0238 | 0.00002 | 0.99334 |
| 73 | A*1107 | 0.00002 | 0.99336 |
| 74 | A*2484 | 0.00002 | 0.99338 |
| 75 | A*2414 | 0.00002 | 0.99340 |
| 76 | A*2417 | 0.00002 | 0.99342 |
| 77 | A*2431 | 0.00002 | 0.99344 |
| 78 | A*2441 | 0.00002 | 0.99346 |
| 79 | A*3109 | 0.00002 | 0.99348 |
| 80 | A*3203 | 0.00002 | 0.99350 |
| 81 | A*3307 | 0.00002 | 0.99352 |
| 82 | A*7402 | 0.00002 | 0.99354 |

TABLE 3

List of 139 alleles of the group HLA-B alleles and frequencies in 7 Asian population

| No. | HLA-B | Frequency | Accumulative |
|---|---|---|---|
| 1 | B*4001 | 0.1335 | 0.1335 |
| 2 | B*4601 | 0.1104 | 0.2439 |
| 3 | B*5801 | 0.0856 | 0.3295 |
| 4 | B*1502 | 0.0733 | 0.4028 |
| 5 | B*3802 | 0.0658 | 0.4686 |
| 6 | B*1301 | 0.0637 | 0.5323 |
| 7 | B*5101 | 0.0492 | 0.5815 |
| 8 | B*1501 | 0.0439 | 0.6254 |
| 9 | B*5401 | 0.0248 | 0.6502 |
| 10 | B*4403 | 0.0221 | 0.6723 |
| 11 | B*3501 | 0.0207 | 0.6930 |
| 12 | B*4801 | 0.0204 | 0.7134 |
| 13 | B*1302 | 0.0203 | 0.7337 |
| 14 | B*5501 | 0.0173 | 0.7510 |
| 15 | B*3801 | 0.0173 | 0.7683 |
| 16 | B*0705 | 0.0173 | 0.7856 |
| 17 | B*4002 | 0.0156 | 0.8012 |
| 18 | B*4006 | 0.0139 | 0.8151 |
| 19 | B*4803 | 0.0134 | 0.8285 |
| 20 | B*5102 | 0.0134 | 0.8419 |
| 21 | B*3901 | 0.0128 | 0.8547 |

TABLE 3-continued

List of 139 alleles of the group HLA-B alleles and frequencies in 7 Asian population

| No. | HLA-B | Frequency | Accumulative |
|---|---|---|---|
| 22 | B*1801 | 0.0123 | 0.8670 |
| 23 | B*2704 | 0.0118 | 0.8788 |
| 24 | B*3505 | 0.0107 | 0.8895 |
| 25 | B*1525 | 0.0096 | 0.8991 |
| 26 | B*5201 | 0.0093 | 0.9084 |
| 27 | B*0702 | 0.0093 | 0.9177 |
| 28 | B*5601 | 0.0087 | 0.9264 |
| 29 | B*1518 | 0.0059 | 0.9323 |
| 30 | B*3503 | 0.0040 | 0.9363 |
| 31 | B*1513 | 0.0040 | 0.9403 |
| 32 | B*6701 | 0.0039 | 0.9442 |
| 33 | B*4501 | 0.0037 | 0.9479 |
| 34 | B*5901 | 0.0025 | 0.9504 |
| 35 | B*1511 | 0.0024 | 0.9528 |
| 36 | B*1521 | 0.0024 | 0.9552 |
| 37 | B*1401 | 0.0023 | 0.9575 |
| 38 | B*1802 | 0.0020 | 0.9595 |
| 39 | B*4010 | 0.0021 | 0.9616 |
| 40 | B*5001 | 0.0020 | 0.9636 |
| 41 | B*1527 | 0.0019 | 0.9655 |
| 42 | B*5604 | 0.0018 | 0.9673 |
| 43 | B*3508 | 0.0018 | 0.9691 |
| 44 | B*3906 | 0.0019 | 0.9710 |
| 45 | B*1505 | 0.0018 | 0.9728 |
| 46 | B*3909 | 0.0018 | 0.9746 |
| 47 | B*5603 | 0.0018 | 0.9764 |
| 48 | B*7802 | 0.0018 | 0.9782 |
| 49 | B*1503 | 0.0018 | 0.9800 |
| 50 | B*1803 | 0.0018 | 0.9818 |
| 51 | B*3907 | 0.0018 | 0.9836 |
| 52 | B*3911 | 0.0018 | 0.9854 |
| 53 | B*2706 | 0.0015 | 0.9869 |
| 54 | B*5502 | 0.0012 | 0.9881 |
| 55 | B*3701 | 0.0008 | 0.9889 |
| 56 | B*5701 | 0.0008 | 0.9897 |
| 57 | B*2705 | 0.0006 | 0.9903 |
| 58 | B*1512 | 0.0006 | 0.9909 |
| 59 | B*0801 | 0.0003 | 0.9912 |
| 60 | B*4402 | 0.0004 | 0.9916 |
| 61 | B*2700 | 0.0004 | 0.9920 |
| 62 | B*1507 | 0.0003 | 0.9923 |
| 63 | B*5602 | 0.0003 | 0.9926 |
| 64 | B*1517 | 0.0002 | 0.9928 |
| 65 | B*1532 | 0.0002 | 0.9930 |
| 66 | B*4101 | 0.0001 | 0.9931 |
| 67 | B*4003 | 0.0001 | 0.9932 |
| 68 | B*3502 | 0.0001 | 0.9933 |
| 69 | B*3915 | 0.0001 | 0.9934 |
| 70 | B*1535 | 0.0001 | 0.9935 |
| 71 | B*2703 | 0.0001 | 0.9936 |
| 72 | B*3530 | 0.0001 | 0.9937 |
| 73 | B*1510 | 0.00007 | 0.99377 |
| 74 | B*4053 | 0.00005 | 0.99382 |
| 75 | B*1506 | 0.00005 | 0.99387 |
| 76 | B*1520 | 0.00005 | 0.99392 |
| 77 | B*1809 | 0.00005 | 0.99397 |
| 78 | B*1811 | 0.00005 | 0.99402 |
| 79 | B*4004 | 0.00005 | 0.99407 |
| 80 | B*4049 | 0.00005 | 0.99412 |
| 81 | B*4201 | 0.00005 | 0.99417 |
| 82 | B*4804 | 0.00005 | 0.99422 |
| 83 | B*4901 | 0.00005 | 0.99427 |
| 84 | B*5507 | 0.00004 | 0.99431 |
| 85 | B*3904 | 0.00004 | 0.99435 |
| 86 | B*5504 | 0.00003 | 0.99438 |
| 87 | B*3902 | 0.00003 | 0.99441 |
| 88 | B*5607 | 0.00003 | 0.99444 |
| 89 | B*1402 | 0.00003 | 0.99447 |
| 90 | B*3905 | 0.00002 | 0.99449 |
| 91 | B*4052 | 0.00003 | 0.99452 |
| 92 | B*5211 | 0.00002 | 0.99454 |
| 93 | B*0740 | 0.00003 | 0.99457 |
| 94 | B*0753 | 0.00002 | 0.99459 |
| 95 | B*1306 | 0.00003 | 0.99462 |
| 96 | B*1309 | 0.00002 | 0.99464 |
| 97 | B*1529 | 0.00002 | 0.99466 |
| 98 | B*1544 | 0.00003 | 0.99469 |
| 99 | B*1581 | 0.00002 | 0.99471 |
| 100 | B*1588 | 0.00003 | 0.99474 |
| 101 | B*1804 | 0.00002 | 0.99476 |
| 102 | B*1805 | 0.00003 | 0.99479 |
| 103 | B*1818 | 0.00002 | 0.99481 |
| 103 | B*2707 | 0.00002 | 0.99483 |
| 105 | B*3507 | 0.00003 | 0.99486 |
| 106 | B*3534 | 0.00002 | 0.99488 |
| 107 | B*3558 | 0.00003 | 0.99491 |
| 108 | B*3572 | 0.00002 | 0.99493 |
| 109 | B*4022 | 0.00003 | 0.99496 |
| 110 | B*4446 | 0.00002 | 0.99498 |
| 111 | B*5108 | 0.00002 | 0.99500 |
| 112 | B*5505 | 0.00003 | 0.99503 |
| 113 | B*5511 | 0.00002 | 0.99505 |
| 114 | B*5606 | 0.00003 | 0.99508 |
| 115 | B*5819 | 0.00002 | 0.99510 |
| 116 | B*7301 | 0.00003 | 0.99513 |
| 117 | B*5106 | 0.00002 | 0.99515 |
| 118 | B*5518 | 0.00002 | 0.99517 |
| 119 | B*1538 | 0.00003 | 0.99520 |
| 120 | B*8101 | 0.00002 | 0.99522 |
| 121 | B*4701 | 0.00002 | 0.99524 |
| 122 | B*3923 | 0.00001 | 0.99525 |
| 123 | B*1528 | 0.000004 | 0.995254 |
| 124 | B*4050 | 0.000001 | 0.995255 |
| 125 | B*4007 | 0.000001 | 0.995256 |
| 126 | B*0731 | 0.000001 | 0.995257 |
| 127 | B*1526 | 0.0000007 | 0.9952577 |
| 128 | B*3504 | 0.0000005 | 0.9952582 |
| 129 | B*3535 | 0.0000005 | 0.9952587 |
| 130 | B*3564 | 0.0000005 | 0.9952592 |
| 131 | B*4011 | 0.0000005 | 0.9952597 |
| 132 | B*4102 | 0.0000005 | 0.9952602 |
| 133 | B*4602 | 0.0000005 | 0.9952607 |
| 134 | B*5103 | 0.0000005 | 0.9952612 |
| 135 | B*5136 | 0.0000005 | 0.9952617 |
| 136 | B*5205 | 0.0000004 | 0.9952621 |
| 137 | B*5301 | 0.0000005 | 0.9952626 |
| 138 | B*5421 | 0.0000005 | 0.9952631 |
| 139 | B*5512 | 0.0000006 | 0.9952636 |

TABLE 4

List of 69 alleles of the group HLA-C alleles and frequencies in 7 Asian population

| No. | HLA-C | Frequency | Accumulative |
|---|---|---|---|
| 1 | C*0102 | 0.1694 | 0.1694 |
| 2 | C*0702 | 0.1266 | 0.2960 |
| 3 | C*0304 | 0.1229 | 0.4189 |
| 4 | C*0801 | 0.1177 | 0.5366 |
| 5 | C*0303 | 0.1044 | 0.6410 |
| 6 | C*1202 | 0.0795 | 0.7205 |
| 7 | C*1402 | 0.0669 | 0.7874 |
| 8 | C*1403 | 0.0620 | 0.8494 |
| 9 | C*0401 | 0.0473 | 0.8967 |
| 10 | C*1502 | 0.0308 | 0.9275 |
| 11 | C*0704 | 0.0132 | 0.9407 |
| 12 | C*0803 | 0.0131 | 0.9538 |
| 13 | C*0302 | 0.0127 | 0.9665 |
| 14 | C*0602 | 0.0107 | 0.9772 |
| 15 | C*0701 | 0.0061 | 0.9833 |
| 16 | C*0403 | 0.0042 | 0.9875 |
| 17 | C*0501 | 0.0037 | 0.9912 |
| 18 | C*0103 | 0.0029 | 0.9941 |
| 19 | C*1203 | 0.0018 | 0.9959 |
| 20 | C*1505 | 0.0010 | 0.9969 |
| 21 | C*0802 | 0.0008 | 0.9977 |

TABLE 4-continued

List of 69 alleles of the group HLA-C alleles and frequencies in 7 Asian population

| No. | HLA-C | Frequency | Accumulative |
|---|---|---|---|
| 22 | C*0202 | 0.0006 | 0.9983 |
| 23 | C*0406 | 0.0005 | 0.9988 |
| 24 | C*0705 | 0.0003 | 0.9991 |
| 25 | C*1602 | 0.0002 | 0.9993 |
| 26 | C*1701 | 0.0002 | 0.9995 |
| 27 | C*1504 | 0.0002 | 0.9997 |
| 28 | C*0810 | 0.0002 | 0.9999 |
| 29 | C*0106 | 0.0001 | 1.0000 |
| 30 | C*0316 | 0.0001 | 1.0001 |
| 31 | C*0411 | 0.0001 | 1.0002 |
| 32 | C*0323 | 0.0001 | 1.0003 |
| 33 | C*0343 | 0.0001 | 1.0004 |
| 34 | C*0715 | 0.0001 | 1.0005 |
| 35 | C*0416 | 0.00007 | 1.00057 |
| 36 | C*0425 | 0.00007 | 1.00063 |
| 37 | C*0727 | 0.00007 | 1.00070 |
| 38 | C*0415 | 0.00007 | 1.00077 |
| 39 | C*0410 | 0.00005 | 1.00082 |
| 40 | C*0721 | 0.00005 | 1.00087 |
| 41 | C*0744 | 0.00005 | 1.00092 |
| 42 | C*0748 | 0.00005 | 1.00097 |
| 43 | C*0808 | 0.00005 | 1.00102 |
| 44 | C*0364 | 0.00004 | 1.00106 |
| 45 | C*1510 | 0.00004 | 1.00111 |
| 46 | C*1604 | 0.00004 | 1.00115 |
| 47 | C*0117 | 0.00003 | 1.00118 |
| 48 | C*0305 | 0.00003 | 1.00120 |
| 49 | C*0308 | 0.00003 | 1.00123 |
| 50 | C*0346 | 0.00003 | 1.00126 |
| 51 | C*0404 | 0.00003 | 1.00128 |
| 52 | C*0424 | 0.00003 | 1.00131 |
| 53 | C*0431 | 0.00003 | 1.00134 |
| 54 | C*0520 | 0.00003 | 1.00137 |
| 55 | C*0611 | 0.00003 | 1.00140 |
| 56 | C*0712 | 0.00003 | 1.00143 |
| 57 | C*0716 | 0.00003 | 1.00146 |
| 58 | C*0719 | 0.00003 | 1.00149 |
| 59 | C*0724 | 0.00003 | 1.00152 |
| 60 | C*0733 | 0.00003 | 1.00155 |
| 61 | C*0749 | 0.00003 | 1.00158 |
| 62 | C*0816 | 0.00003 | 1.00161 |
| 63 | C*1204 | 0.00003 | 1.00164 |
| 64 | C*1209 | 0.00003 | 1.00167 |
| 65 | C*1216 | 0.00003 | 1.00170 |
| 66 | C*1507 | 0.00003 | 1.00173 |
| 67 | C*0317 | 0.00002 | 1.00175 |
| 68 | C*0482 | 0.00002 | 1.00177 |
| 69 | C*0706 | 0.00002 | 1.00179 |

TABLE 5

List of 25 alleles of the group HLA-DQB1 alleles and frequencies in Vietnamese population

| No. | DQB1 | Frequency | Accumulative |
|---|---|---|---|
| 1 | DQB1*0301 | 0.287 | 0.287 |
| 2 | DQB1*0303 | 0.129 | 0.416 |
| 3 | DQB1*0501 | 0.109 | 0.525 |
| 4 | DQB1*0502 | 0.099 | 0.624 |
| 5 | DQB1*0601 | 0.084 | 0.708 |
| 6 | DQB1*0201 | 0.069 | 0.777 |
| 7 | DQB1*0401 | 0.050 | 0.827 |
| 8 | DQB1*0302 | 0.025 | 0.852 |
| 9 | DQB1*0503 | 0.025 | 0.877 |
| 10 | DQB1*0202 | 0.020 | 0.897 |
| 11 | DQB1*0402 | 0.0099 | 0.9069 |
| 12 | DQB1*0501 | 0.0099 | 0.9168 |
| 13 | DQB1*0502 | 0.0099 | 0.9267 |
| 14 | DQB1*0518 | 0.0099 | 0.9366 |
| 15 | DQB1*0602 | 0.0099 | 0.9465 |
| 16 | DQB1*0609 | 0.0099 | 0.9564 |
| 17 | DQB1*0303 | 0.00495 | 0.96135 |
| 18 | DQB1*0305 | 0.00495 | 0.96630 |
| 19 | DQB1*0501 | 0.00495 | 0.97125 |
| 20 | DQB1*0502 | 0.00495 | 0.97620 |
| 21 | DQB1*0503 | 0.00495 | 0.98115 |
| 22 | DQB1*0503 | 0.00495 | 0.98610 |
| 23 | DQB1*0510 | 0.00495 | 0.99105 |
| 24 | DQB1*0603 | 0.00495 | 0.99600 |
| 25 | DQB1*0604 | 0.00495 | 1.00095 |

TABLE 6

List of 26 alleles of the group HLA-DRB1 alleles and frequencies in Vietnamese population

| No. | DRB1 | Frequency | Accumulative |
|---|---|---|---|
| 1 | DRB1*0901 | 0.134 | 0.134 |
| 2 | DRB1*1202 | 0.223 | 0.357 |
| 3 | DRB1*1502 | 0.099 | 0.456 |
| 4 | DRB1*1001 | 0.079 | 0.535 |
| 5 | DRB1*0301 | 0.074 | 0.609 |
| 6 | DRB1*0405 | 0.064 | 0.673 |
| 7 | DRB1*0803 | 0.054 | 0.727 |
| 8 | DRB1*1602 | 0.045 | 0.772 |
| 9 | DRB1*0701 | 0.030 | 0.802 |
| 10 | DRB1*1312 | 0.030 | 0.832 |
| 11 | DRB1*1101 | 0.025 | 0.857 |
| 12 | DRB1*1501 | 0.025 | 0.882 |
| 13 | DRB1*0403 | 0.015 | 0.897 |
| 14 | DRB1*1106 | 0.015 | 0.912 |
| 15 | DRB1*1302 | 0.015 | 0.927 |
| 16 | DRB1*1454 | 0.015 | 0.942 |
| 17 | DRB1*0406 | 0.0099 | 0.9519 |
| 18 | DRB1*1405 | 0.0099 | 0.9618 |
| 19 | DRB1*0401 | 0.00495 | 0.96675 |
| 20 | DRB1*0812 | 0.00495 | 0.9717 |
| 21 | DRB1*1112 | 0.00495 | 0.97665 |
| 22 | DRB1*1301 | 0.00495 | 0.9816 |
| 23 | DRB1*1404 | 0.00495 | 0.98655 |
| 24 | DRB1*1410 | 0.00495 | 0.9915 |
| 25 | DRB1*1418 | 0.00495 | 0.99645 |
| 26 | DRB1*1502 | 0.00495 | 1.0014 |

Figure 2A:
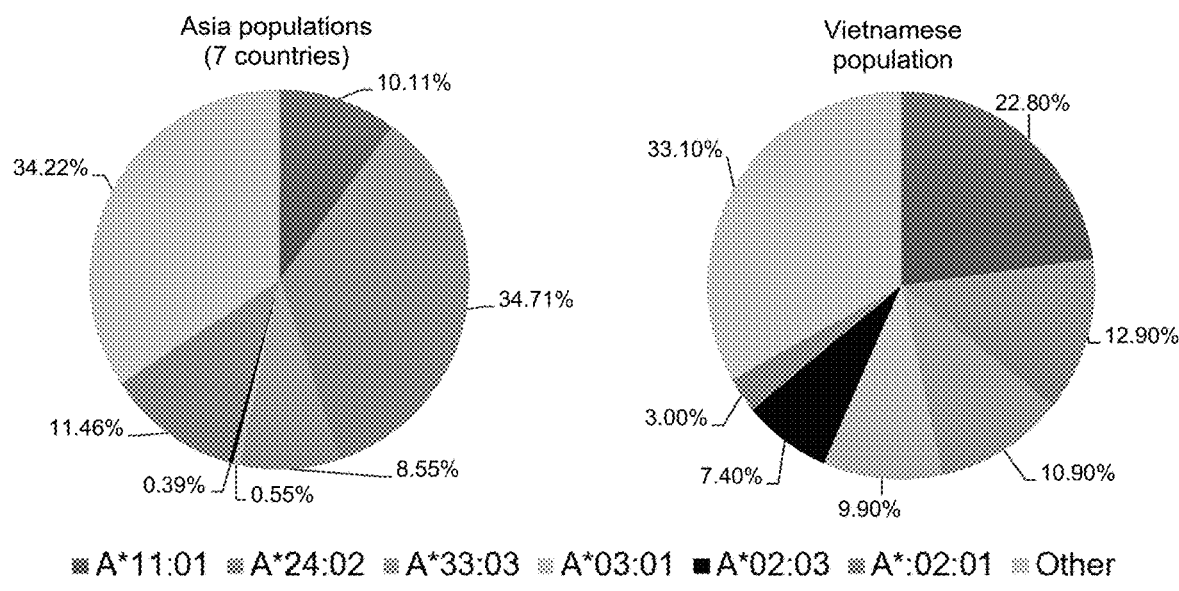
FIG. 2A is a graph illustrated the frequency (%) of alleles belonging to HLA-A allele groups.

According to the preferred embodiment of the present invention, the group HLA-A types alleles include A*1101, A*0201, A*0203, A*2402, A*0301, and A*3303; all of these alleles have frequencies (%) listed in Table 7 below and are illustrated by graph the reference by FIG. 2A.

TABLE 7

HLA-A allele frequency of each Asian population is selected from 07 countries

|  | A*1101 | A*0201 | A*0203 | A*2402 | A*0301 | A*3303 | Other |
|---|---|---|---|---|---|---|---|
| China Canton Han (n = 264) | 26.7% | 15.3% | 11.2% | 16.3% | 1.7% | 0% | 28.8% |
| Indonesia Sundanese and Javanese (n = 201) | 16.4% | 7.5% | 3.7% | 14.4% | 2.5% | 16.9% | 38.6% |
| Japan (n = 18604) | 9.1% | 11.6% | 0.063% | 36.5% | 0.396% | 7.5% | 34.841% |
| Malaysia Peninsular Malay (n = 951) | 17.1% | 6.1% | 2.2% | 19.8% | 1.1% | 4.2% | 49.5% |
| Vietnam Kinh (n = 101) | 22.8% | 3% | 7.4% | 12.9% | 0.495% | 10.9% | 42.505% |
| South Korea (n = 485) | 10.8% | 16.5% | 0.5% | 21.7% | 1.8% | 16.3% | 32.4% |
| Thailand (n = 142) | 29.9% | 1.8% | 7.7% | 3.9% | 0.7% | 0% | 56% |
| Vietnam Hanoi Kinh (n = 170) | 22.9% | 2.1% | 7.9% | 13.8% | 0% | 11.5% | 41.8% |

Figure 2B:
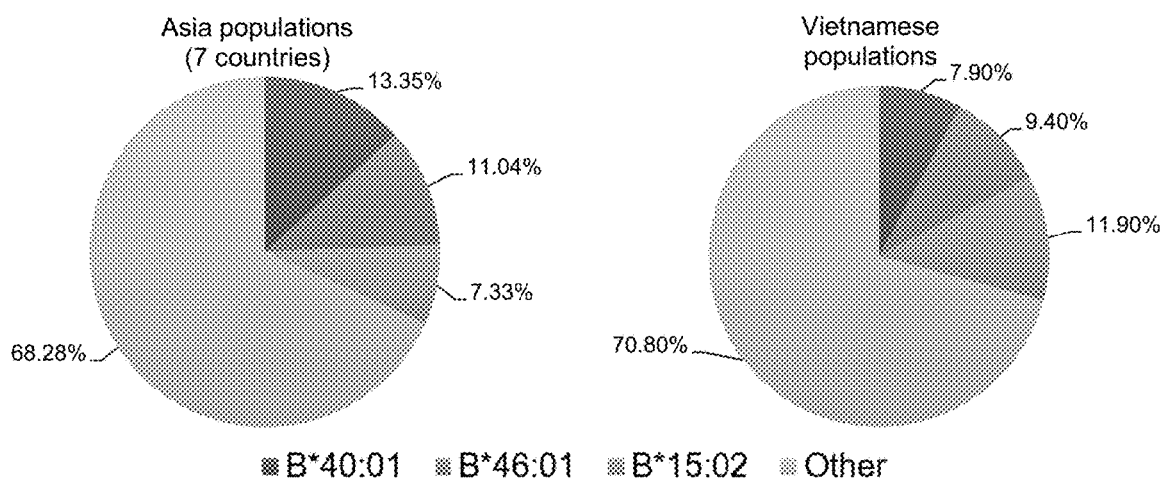
FIG. 2B is a graph illustrated the frequency (%) of alleles belonging to HLA-B allele groups.

According to the preferred embodiment of the present invention, the group HLA-B types alleles include B*1502, B*4001, and B*4601; all of these alleles have frequencies (%) listed in Table 8 below and are illustrated by graph the reference by FIG. 2B.

TABLE 8

HLA-B allele frequency of each Asian population is selected from 07 countries

|  | B*1502 | B*4001 | B*4601 | Other |
|---|---|---|---|---|
| China Canton Han (n = 264) | 7.3% | 14.4% | 11.9% | 66.4% |
| Indonesia Sundanese and Javanese (n = 201) | 10.7% | 3.5% | 0% | 85.8% |
| Japan (n = 18604) | 0.031% | 5.3% | 4.8% | 89.869% |
| Malaysia Peninsular Malay (n = 951) | 12.3% | 3.6% | 2.5% | 81.6% |
| Vietnam Kinh (n = 101) | 11.9% | 7.9% | 9.4% | 70.8% |
| South Korea (n = 485) | 0.2% | 4% | 4.4% | 91.4% |
| Thailand (n = 142) | 8.5% | 8.5% | 9.2% | 73.8% |
| Vietnam Hanoi Kinh (n = 170) | 13.5% | 6.2% | 11.5% | 68.8% |

Figure 2C:
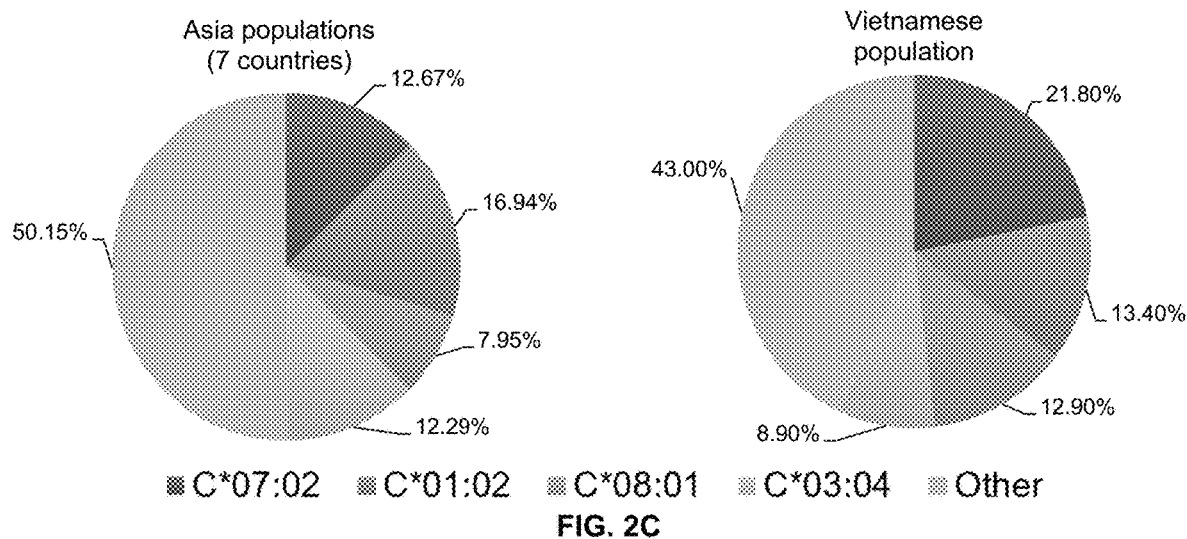
FIG. 2C is a graph illustrated the frequency (%) of alleles belonging to HLA-C allele groups.

According to the preferred embodiment of the present invention, the group HLA-C types alleles include C*0102, C*0702, C*0801, and C*0304; all of these alleles have frequencies (%) listed in Table 9 below and are illustrated by graph the reference by FIG. 2C.

TABLE 9

HLA-C allele frequency of each Asian population is selected from 07 countries

|  | C*0102 | C*0702 | C*0801 | C*0304 | Other |
|---|---|---|---|---|---|
| China Canton Han (n = 264) | 17.4% | 2.1% | 13.3% | 11.2% | 37.1% |
| Indonesia Sundanese and Javanese (n = 201) | 0% | 0% | 0% | 0% | 100% |
| Japan (n = 18604) | 17.6% | 12.7% | 7.4% | 12.4% | 49.9% |
| Malaysia Peninsular Malay (n = 951) | 4.4% | 10.9% | 16.4% | 4.3% | 64% |
| Vietnam Kinh (n = 101) | 13.4% | 21.8% | 12.9% | 7.4% | 44.5% |
| South Korea (n = 485) | 18.3% | 8.3% | 7.4% | 3.9% | 62.1% |
| Thailand (n = 142) | 11.6% | 13% | 12% | 9.5% | 53.9% |
| Vietnam Hanoi Kinh (n = 170) | 16.5% | 14.7% | 15.6% | 6.2% | 47% |

Figure 3A:
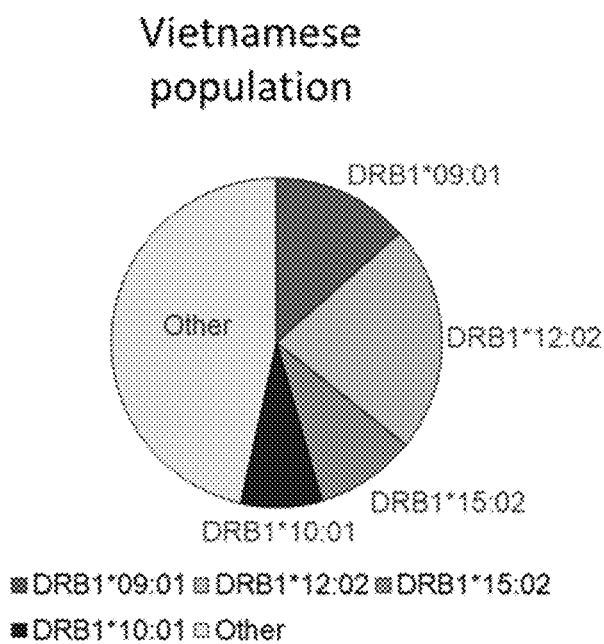
FIG. 3A is a graph illustrated the frequency (%) of alleles belonging to HLA-DRB1 allele groups.

Still at step 120a, the list of 04 most frequent HLA class II types covering 41% Asian population or 50% of Vietnamese population comprising two main group alleles: HLA-DRB1, and HLA-DQB1. The HLA-DRB1 types alleles include DRB1*0901 and DRB1*1202; all of these alleles have frequencies (%) listed in Table 10 below and are illustrated by graph the reference by FIG. 3A.

TABLE 10

DRB1 allele frequency of each Vietnam Kinh and Vietnam Hanoi Kinh

|  | DRB1*0901 | DRB1*1202 | Other |
|---|---|---|---|
| Vietnam Kinh (n = 101) | 15% | 21% | 64% |
| Vietnam Hanoi Kinh (n = 170) | 12.5% | 30% | 57.5% |

Figure 3B:
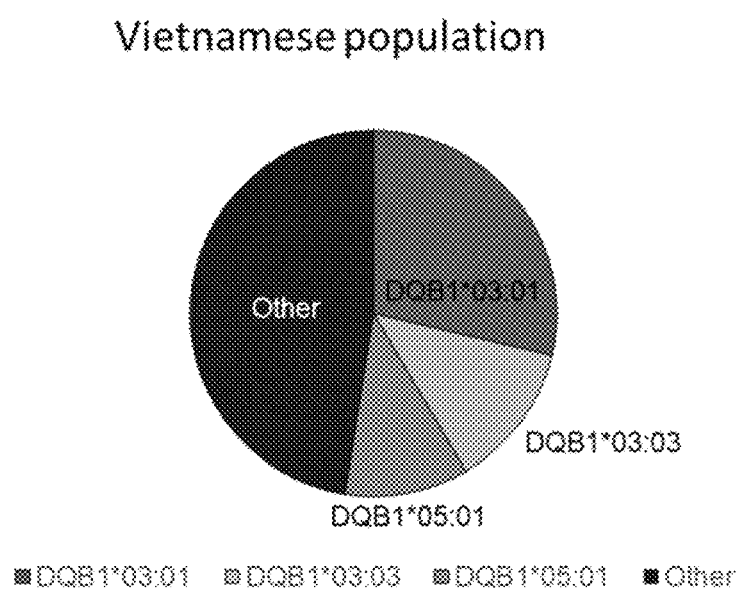
FIG. 3B is a graph illustrated the frequency (%) of alleles belonging to HLA-DQB1 allele groups.

According to the embodiment of the invention, the HLA-DQB1 types alleles include DQB1*0301 and DQB1*0303; all of these alleles have frequencies (%) listed in Table 11 below and are illustrated by graph the reference by FIG. 3B.

TABLE 11

DQB1 allele frequency of each Vietnam Kinh and Vietnam Hanoi Kinh

|  | DQB1*0301 | DQB1*0303 | Other |
|---|---|---|---|
| Vietnam Kinh (n = 101) | 10% | 29% | 61% |
| Vietnam Hanoi Kinh (n = 170) | 15% | 37.5% | 47.5% |

According to the preferred embodiment of the present invention, data of the list of 04 alleles HLA class II access the Database of HLA class II frequency in Kinh population, and referenced by paper: Do M D, Le L G H, Nguyen V T, Dang T N, Nguyen N H, Vu H A, Mai T P. *High-Resolution HLA Typing of HLA-A, HLA-B, HLA-C, HLA-DRB1, and HLA-DQB1 in Kinh Vietnamese by Using Next-Generation Sequencing. Front Genet.* 2020 Apr. 30; 11:383. doi: 10.3389/fgene.2020.00383. PMID: 32425978; PMCID: PMC7204072.

At step 120b, generating the library of aAPC including a library of aAPC by genetically engineering K562 cells to the co-express selected HLA class I types and the co-stimulatory molecule; and a library of aAPC by genetically engineering K562 cells to co-express selected HLA class II types and the co-stimulatory molecule. It should be noted that the term "co-stimulatory molecule" is a heterogenous group of cell surface molecules that act to amplify or counteract the initial activating signals provided to T cells from the T cell receptor (TCR) following its interaction with an antigen/major histocompatibility complex (MHC), thereby influencing T cell differentiation.

According to the preferred embodiment of the present invention, the co-stimulatory molecule is CD80 molecule.

According to the preferred embodiment of the present invention, generation the library of aAPC by genetically engineering K562 cells to the co-express selected HLA class I types and the CD80 molecule according to method 200, which will be described in detail later below.

According to the preferred embodiment of the present invention, generation the library of aAPC by genetically engineering K562 cells to the co-express selected HLA class II types and the CD80 molecule according to method 300, which will be described in detail later below.

Finally, at step 130, using the library of aAPC at step 120 for rapid and comprehensive screening for selecting of immunogenic peptides (neoantigens) from the off-the-shelf peptides at step 110 or TMGs at step 110 that activate T cells via immunological assays (ELISpot or intracellular staining flow cytometry).

According to the embodiment of the present invention, using the library of aAPC co-expressing HLA types and CD80 molecule for screening immunogenic peptides for cancer patients expressing low levels of co-stimulatory receptor CD28 which is required for licensing T cell responses.

According to the preferred embodiment of the present invention, using the library of aAPC for screening and selecting immunogenic peptides (neoantigens) from the off-the-shelf peptides activate T cells within 10 days according to method 400, which will be described in detail later below.

According to the preferred embodiment of the present invention, using the library of aAPC for screening and selecting immunogenic peptides (neoantigens) from TMGs activate T cells within 12 days according to method 500, which will be described in detail later below.

Figure 4:
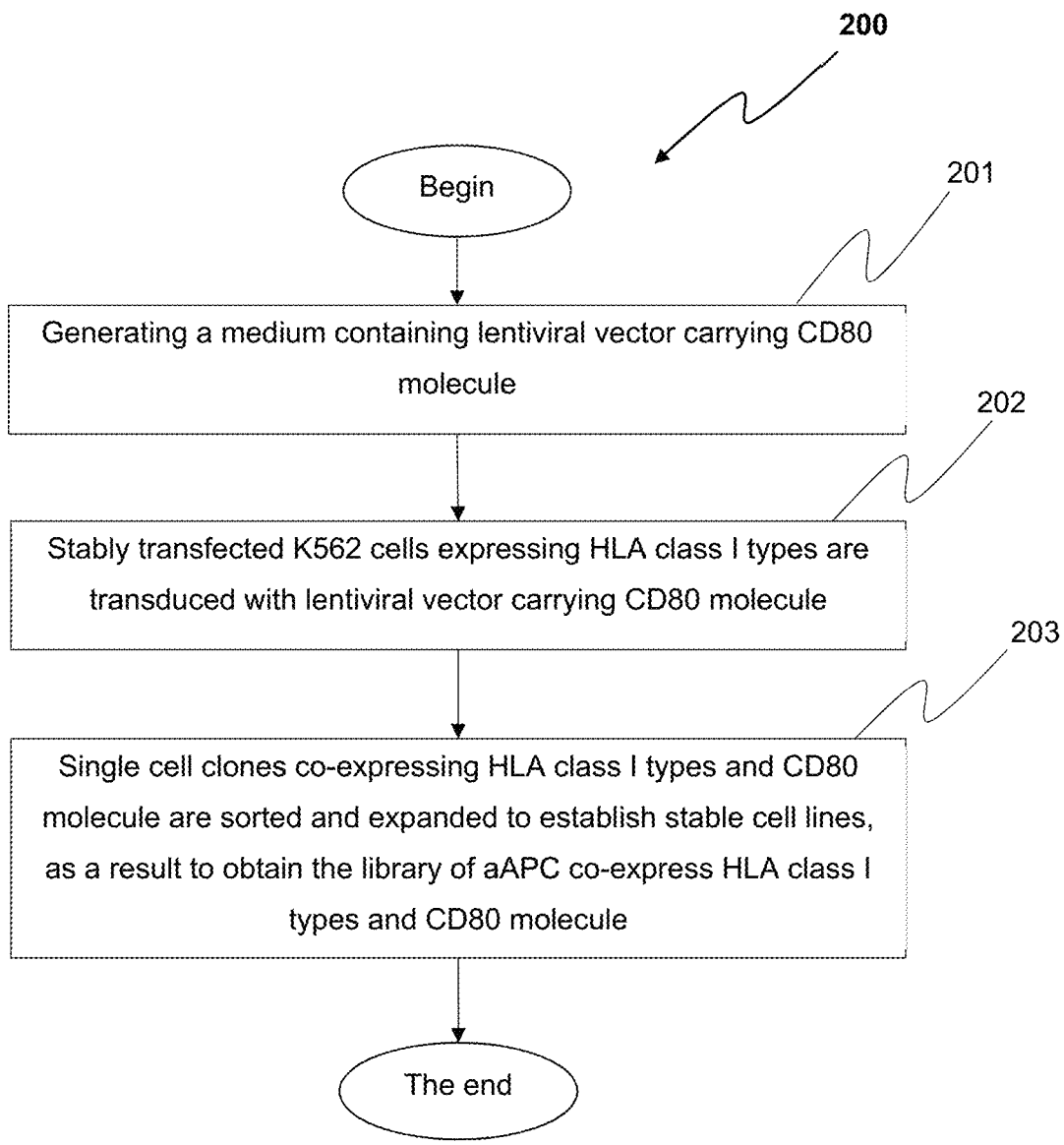
FIG. 4 is a flowchart illustrated a specific method for generating the library of aAPC by genetically engineering K562 cells to co-express HLA class I types and CD80 molecule according to embodiment of the present invention.

Referring to FIG. 4, the method for generating the library of aAPC by genetically engineering K562 cells to co-express HLA class I types and CD80 molecule 200 ("method 200") in accordance embodiment of the present invention. In particular, method 200 includes the following steps:

At step 201, generating a medium containing lentiviral vector carrying CD80 molecule by performing the steps in the following order:
- $8 \times 10^6$ Lenti-X 293T cells (Clontech) are seeded into 10 cm$^2$ plate for 24 hours prior to transfection in Dulbecco's Modified Eagle Medium (DMEM; Gibco) supplemented with 10% FBS, 100 units/ml penicillin, and 100 μg/ml streptomycin at 37° C. in a humidified 5% $CO_2$ incubator;
- Third generation lentivirus helper plasmids (RSV packaging plasmid, MDIg regulatory plasmid, and MD2G envelope plasmid) and pLT-CD80 transfer plasmid are co-transfected into Lenti-X 293T cell line to produce lentiviral vector particles using 293Fectin (ThermoFisher) according to manufacturer's instructions;
- At 6 hours post-transfection, the medium is replaced with fresh medium; and
- After 72 hours, the medium containing lentiviral vector carrying CD80 molecule is collected in conical tubes and stored at 4° C. for short-term, and at −80° C. for long-term storage.

At step 202, stably transfected K562 cells expressing HLA class I types are transduced with lentiviral vector carrying CD80 molecule, adding polybrene (8 ug/mL) in 24 well-plate; wherein each plate is centrifuged at 1000×g for 30 mins.

Finally, at step 203, single cell clones co-expressing HLA class I types and CD80 molecule are sorted and expanded to establish stable cell lines. As a result, to obtain the library of aAPC co-express HLA class I types and CD80 molecule.

Figure 5:
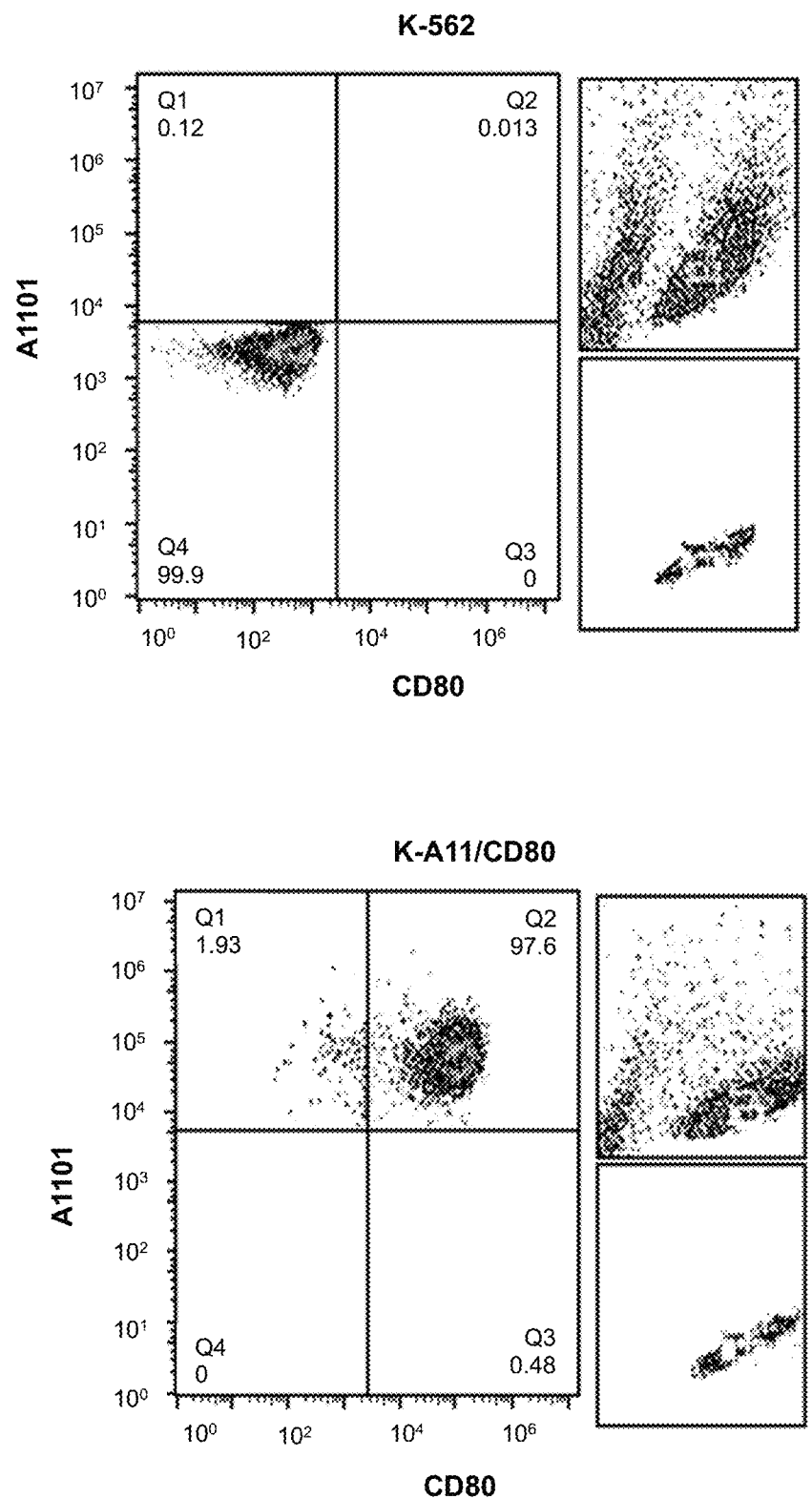
FIG. 5 is an image illustrated expression of HLA-A1101 and CD80 molecule in K562 in accordance with an exemplary embodiment of the present invention.

According to an exemplary embodiment of the invention, referring to FIG. 5 is an image illustrated expression of HLA-A1101 and CD80 molecule in K562.

Figure 6:
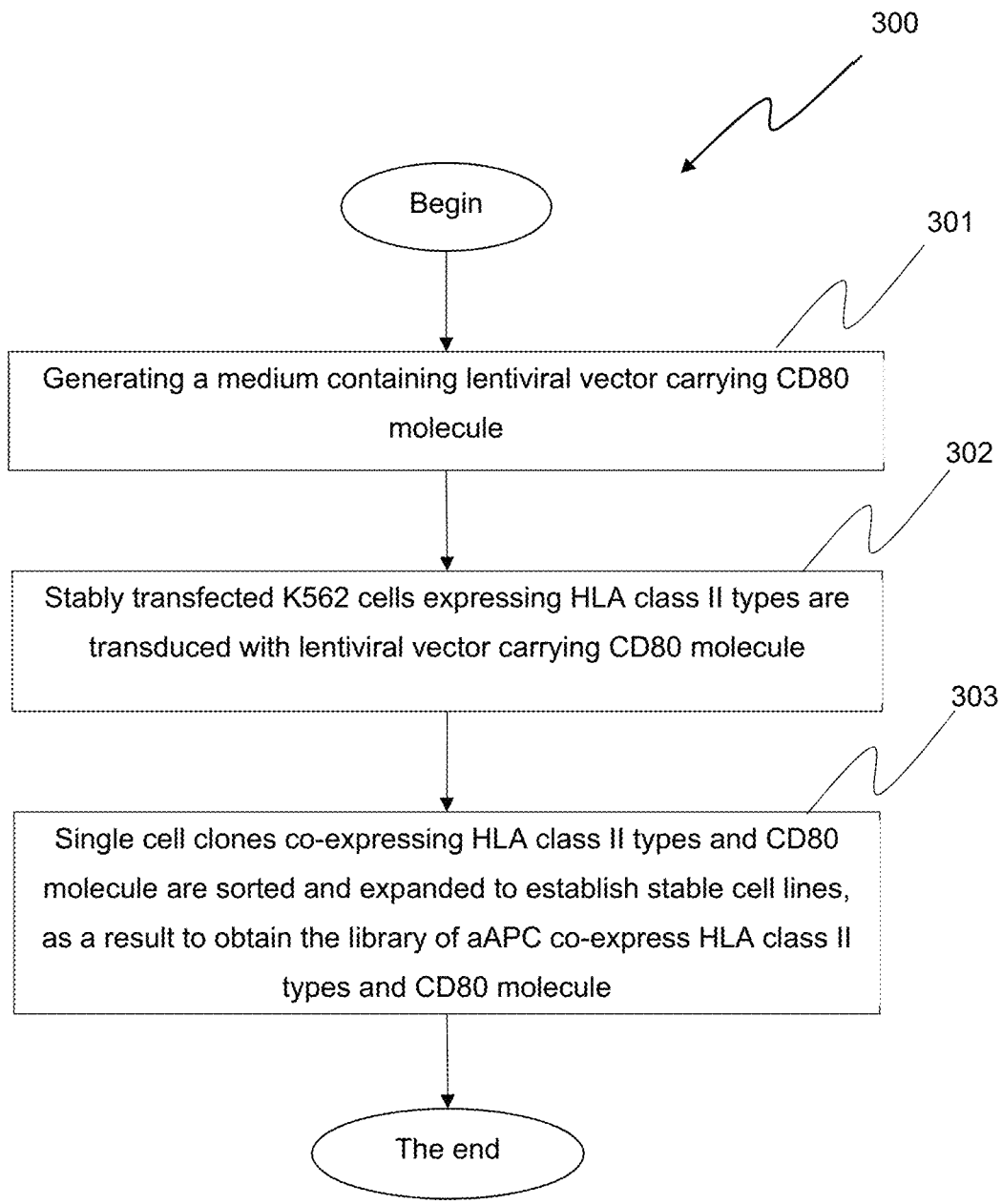
FIG. 6 is a flowchart illustrated a specific method for generating the library of aAPC by genetically engineering K562 cells to co-express HLA class II types and CD80 molecule according to embodiment of the present invention.

Referring to FIG. 6, the method for generating the library of aAPC by genetically engineering K562 cells to co-express HLA class II types and CD80 molecule 300 ("method 300") in accordance embodiment of the present invention. In particular, method 300 includes the following steps:

At step 301, generating a medium containing lentiviral vector carrying CD80 molecule by performing the steps in the following order:
- $8 \times 10^6$ Lenti-X 293T cells (Clontech) are seeded into 10 cm$^2$ plate for 24 hours prior to transfection in Dulbecco's Modified Eagle Medium (DMEM; Gibco) supplemented with 10% FBS, 100 units/ml penicillin, and 100 μg/ml streptomycin at 37° C. in a humidified 5% $CO_2$ incubator;
- Third generation lentivirus helper plasmids (RSV packaging plasmid, MDIg regulatory plasmid, and MD2G envelope plasmid) and pLT-CD80 transfer plasmid are co-transfected into Lenti-X 293T cell line to produce lentiviral vector particles using 293Fectin (ThermoFisher) according to manufacturer's instructions;
- At 6 hours post-transfection, the medium is replaced with fresh medium; and
- After 72 hours, the medium containing lentiviral vector carrying CD80 molecule is collected in conical tubes and stored at 4° C. for short-term, and at −80° C. for long-term storage.

At step 302, stably transfected K562 cells expressing HLA class II types are transduced with lentiviral vector carrying CD80 molecule, adding polybrene (8 ug/mL) in 24 well-plate; wherein each plate is centrifuged at 1000×g for 30 mins.

Finally, at step 203, single cell clones co-expressing HLA class II types and CD80 molecule are sorted and expanded to establish stable cell lines. As a result, to obtain the library of aAPC co-express HLA class II types and CD80 molecule.

Figure 7:
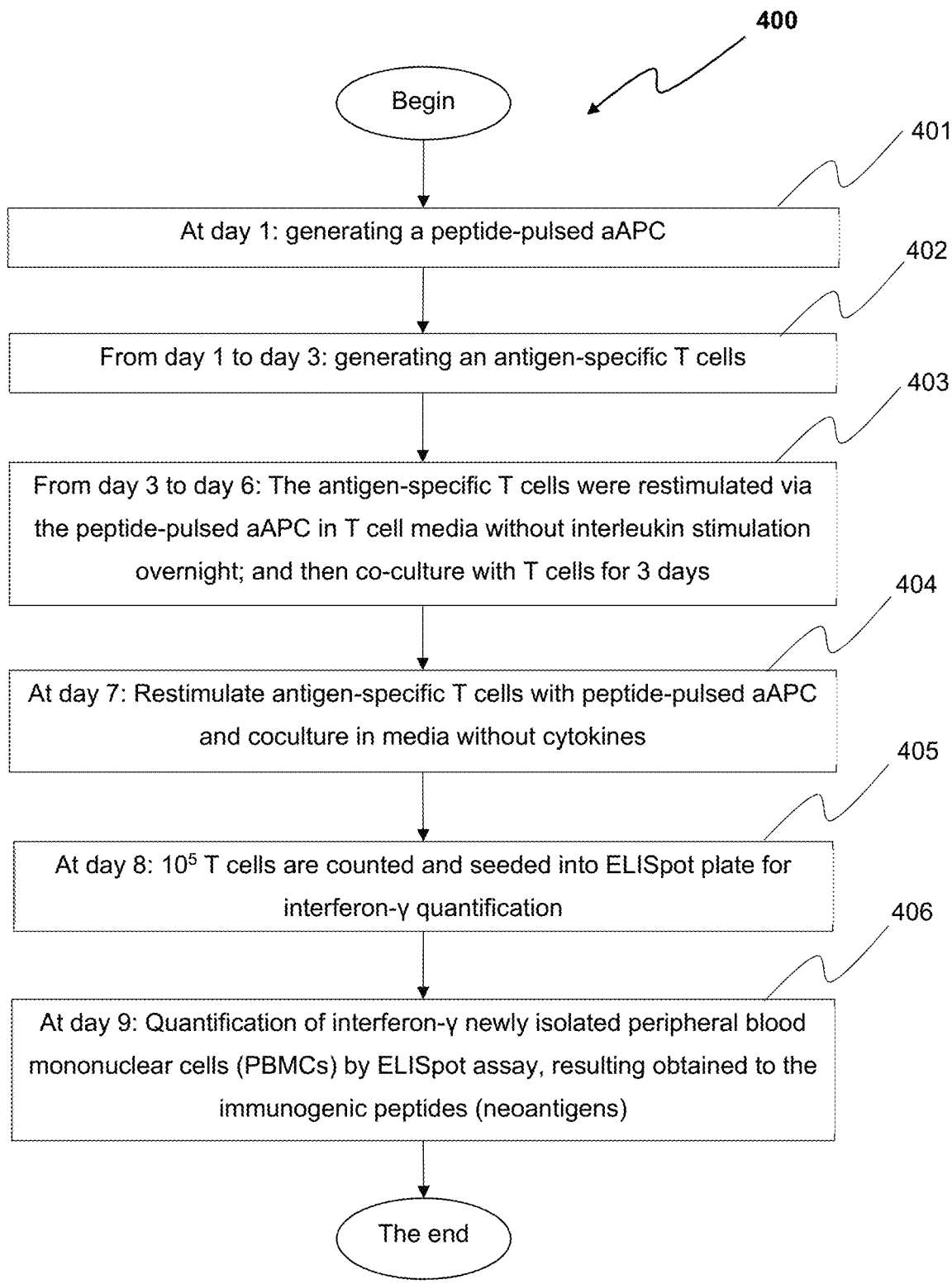
FIG. 7 is a flowchart illustrated a specific method for screening and selecting immunogenic peptides (neoantigens) from the off-the-shelf peptides activate T cells within 9 days by using the library of aAPC according to embodiment of the present invention.

Referring to FIG. 7, the method 400 for screening and selecting immunogenic peptides (neoantigens) from the off-the-shelf peptides activate T cells within 17 days by using the library of aAPC ("method 400") in accordance embodiment of the present invention.

According to the embodiment of the invention, before starting method 400, it is necessary to prepare the off-the-shelf peptides by taking a patient's tumor tissues and whole blood cells, performing targeted sequencing for profiling selected recurrent mutations according the method 100, then comparing and analyzing the mutation profiles of tumor tissues; resulting in obtaining corresponding the off-the-shelf peptides.

Method 400 includes the following steps:

At step 401, at day 1, generating a peptide-pulsed aAPC by performing the steps in the following order:
(a1) T cells isolated from PBMCs of healthy donor carrying appropriated HLA class I or HLA class II type are cultured in AIM-V media supplemented with 10% FBS, and 10 ng/ml of IL-21; and T cells are enriched by CD3 marker;

(b1) Corresponding K562 aAPC cells expressing HLA class I or HLA class II are cultured in RPMI1640 media supplemented with 10% FBS, and 1% PS;
wherein said culture media is exchanged to OptiMEM media without FBS to enhance the exogenous peptide uptake;
wherein 25 µM of each peptide is pulsed with aAPC cells for 3 hours; in which each peptide consists of 25 amino acids covering mutations classified into three tiers of the first collection of off-the-shelf peptides;
(c1) OptiMEM media is removed, and cells are washed two times with PBS; results obtained the peptide-pulsed aAPC.

At step 402, from day 1 to day 3, generating an antigen-specific T cells comprising the following steps:
Fixing the peptide-pulsed aAPC with 0.1% formaldehyde for ten minutes at room temperature (RT);
Washing one time with PBS and one time with culture media to remove formaldehyde; and
Co-culture with T cells in T cell media supplemented IL-7 (10 ng/ml), IL-21 (10 ng/mL), IL-15 (10 ng/mL) at the ratio of 2:1 (T cells: fixed aAPC cells) for 3 days; wherein T cells isolated from PBMCs of healthy donor carrying appropriated HLA class I or HLA class II type are cultured in AIM-V media supplemented with 10% FBS, and 10 ng/ml of IL-21; and T cells are enriched by CD3 marker.

At step 403, from day 3 to day 6, the antigen-specific T cells were restimulated via the peptide-pulsed aAPC at step 402 in T cell media without interleukin stimulation overnight, and then co-culture with T cells in T cell media supplemented IL-7 (10 ng/mL), IL-21 (10 ng/ml), IL-15 (10 ng/ml) for 3 days.

At step 404, at day 7, restimulate antigen-specific T cells with peptide-pulsed aAPC and coculture in media without cytokines.

At step 405, at day 8, $10^5$ T cells are counted and seeded into ELISpot plate for interferon-γ quantification.

Finally, at step 406, at day 9, quantification of interferon-γ newly isolated peripheral blood mononuclear cells (PBMCs) by ELISpot assay, resulting obtained to the immunogenic peptides (neoantigens); wherein based on spots from mutant (MT) peptides and wild type (WT) peptides are measured by ELISpot reader, peptides with MT/WT fold change greater than or equal to 2 (≥2) are defined as immunogenic peptides.

According to the embodiment of the invention, using the library of aAPC for screening immunogenic peptides according the method 400 from the off-the-shelf peptides activate both CD4+ T cells and CD8+ T cells or exclusively activate CD8+ T cells.

According to the preferred embodiment of the present invention, using the library of aAPC for screening immunogenic peptides according the method 400 from the off-the-shelf peptides activate both CD4+ T cells and CD8+ T cells comprising: ATM_p.V60X, ARID1A_p.G1848X, ERG_p.-446-447X, DCTN1_p.R1173H, PIK3CA_p.R357Q, BRAF_p.D634N, BRAF_p.G509V, UBR5_p.R1331C, AMER1_p.F173X, NCOR2_p.P975X, POU2AF1_p.A226V, KRAS_p.G12S, TP53_p.A159P, ELK4_p.S359X, KRAS_p.G12C, RNF43_p.G659X, TP53_p.R248Q, and PIK3CA_p.E545A.

According to the preferred embodiment of the present invention, using the library of aAPC for screening immunogenic peptides according the method 400 from the off-the-shelf peptides exclusively activate CD8+ T cells comprising: TCF7L2_p.H198X, SMAD4_p.G30X, MTOR_p.S2215F, ATP1A1_p.G98X, ARID1A_p.S764SX, ASXL1_p.G643X, GNAS_p.R201C, PIK3CA_p.R88Q, PIK3CA_p.E970K, FBXW7_p.S582L, FBXW7_p.R465H, IL7R_p.K119X, EGFR_p.L858R, AKAP9_p.K37X, KRAS_p.A146T, CHD4_p.K73X, TP53_p.E286K, TP53_p.V157F, BARD1_p.K171X, PIK3CA_p.V344G, PIK3CA_p.E542K, AKAP9_p.SE1650-1651SX, KRAS_p.G13D, KRAS_p.G12V, KRAS_p.G12A, KRAS_p.G12D, TP53_p.R282W, GNAS_p.R201H, and BRAF_p.V640E.

Figure 8:
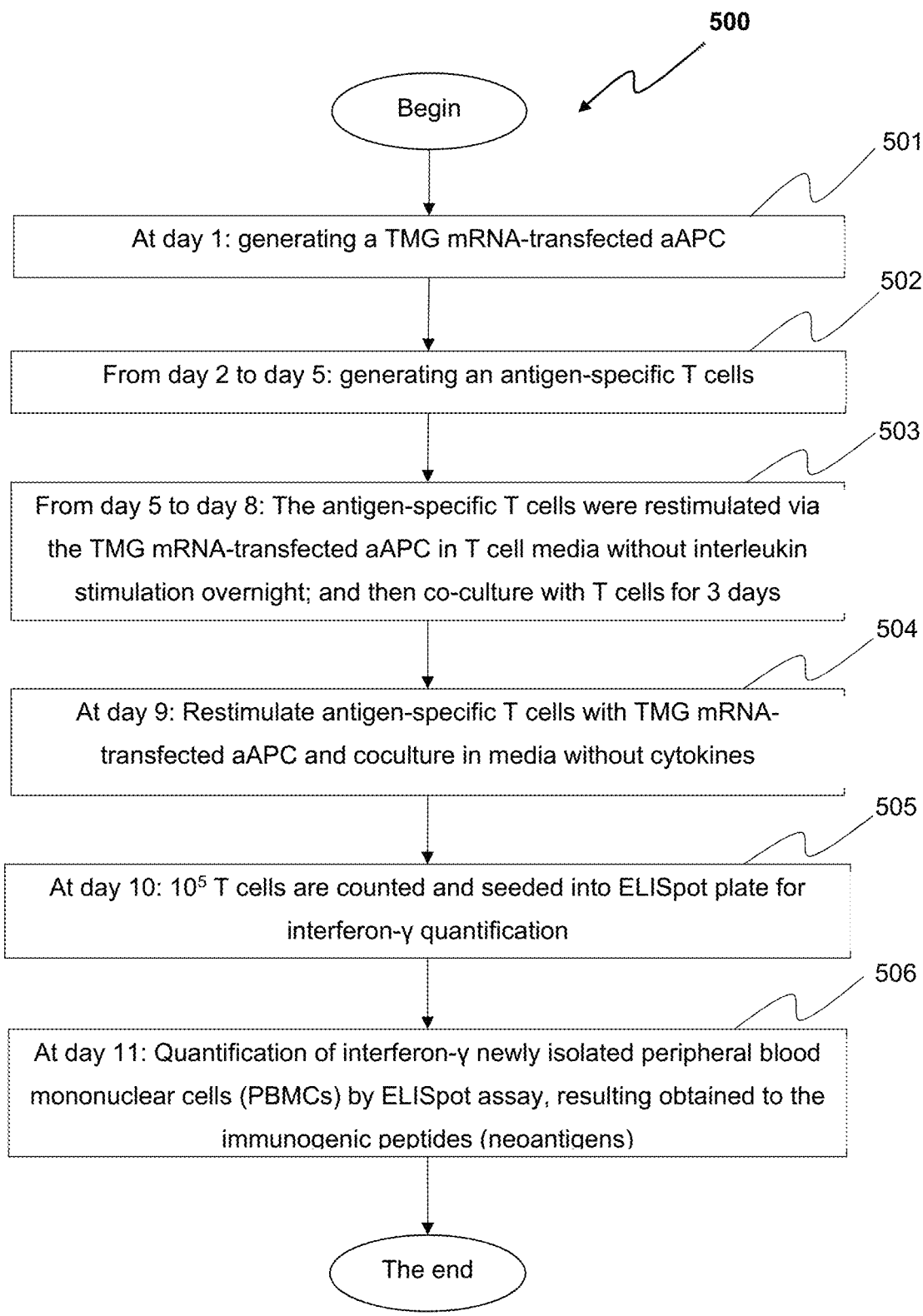
FIG. 8 is a flowchart illustrated a specific method for screening and selecting immunogenic peptides (neoantigens) from TMGs activate T cells within 11 days by using the library of aAPC according to embodiment of the present invention.

In reference to FIG. 8, the method 500 for screening and selecting immunogenic peptides (neoantigens) from TMGs activate T cells within 18 days by using the library of aAPC ("method 500") in accordance embodiment of the present invention.

According to the embodiment of the invention, before starting method 500, it is necessary to prepare the TMGs by taking a patient's tumor tissues and whole blood cells, performing targeted sequencing for profiling selected recurrent mutations according the method 100, then comparing and analyzing the mutation profiles of tumor tissues; resulting in obtaining corresponding the TMGs.

Method 500 includes the following steps:

At step 501, at day 1, generating a TMG mRNA-transfected aAPC by performing the steps in the following order:
(a2) T cells isolated from PBMCs of healthy donor carrying appropriated HLA class I or HLA class II type are cultured in AIM-V media supplemented with 10% FBS, and 10 ng/ml of IL-21; and T cells are enriched by CD3 marker;
(b2) Corresponding K562 aAPC cells expressing HLA class I or HLA class II are cultured in RPMI1640 media supplemented with 10% FBS, and 1% PS;
(c2) TMG mRNAs are invitro synthesized and transfected into K562 aAPC cells by using Lipofectamine MessengerMAX; and then cultured for overnight; results obtained the TMG mRNA-transfected aAPC.

At step 502, from day 2 to day 5, generating an antigen-specific T cells comprising the following steps:
Fixing the TMG mRNA-transfected aAPC with 0.1% formaldehyde for ten minutes at room temperature (RT); and
Washing one time with PBS and one time with culture media to remove formaldehyde; and then co-culture with T cells in T cell media supplemented IL-7 (10 ng/ml), IL-21 (10 ng/ml), IL-15 (10 ng/mL) at the ratio of 2:1 (T cells: fixed aAPC cells) for 3 days; wherein T cells isolated from PBMCs of healthy donor carrying appropriated HLA class I or HLA class II type are cultured in AIM-V media supplemented with 10% FBS, and 10 ng/ml of IL-21; and T cells are enriched by CD3 marker.

At step 503, from day 5 to day 8, the antigen-specific T cells were restimulated via the TMG mRNA-transfected aAPC in T cell media without interleukin stimulation overnight; and then co-culture with T cells in T cell media supplemented IL-7 (10 ng/ml), IL-21 (10 ng/ml), IL-15 (10 ng/ml) for 3 days.

At step 504, at day 9, restimulate antigen-specific T cells with TMG mRNA-transfected aAPC and coculture in media without cytokines.

At step 505, at day 10, $10^5$ T cells are counted and seeded into ELISpot plate for interferon-γ quantification.

Finally, at step 506, at day 11, quantification of interferon-γ newly isolated peripheral blood mononuclear cells (PBMCs) by ELISpot assay, resulting obtained to the immunogenic peptides (neoantigens); wherein based on spots from mutant (MT) TMGs and corresponding wild type (WT)

TMGs are measured by ELISpot reader, peptides with MT/WT fold change greater than or equal to 2 (≥2) are defined as immunogenic peptides.

According to the embodiment of the invention, using the library of aAPC for screening immunogenic peptides according the method 500 from TMGs activate both CD4+ T cells and CD8+ T cells or exclusively activate CD8+ T cells.

According to the preferred embodiment of the present invention, using the library of aAPC for screening immunogenic peptides according the method 500 from TMGs activate both CD4+ T cells and CD8+ T cells comprising: ATM_p.V60X, ARID1A_p.G1848X, ERG_p.-446-447X, DCTN1_p.R1173H, PIK3CA_p.R357Q, BRAF_p.D634N, BRAF_p.G509V, UBR5_p.R1331C, AMER1_p.F173X, NCOR2_p.P975X, POU2AF1_p.A226V, KRAS_p.G12S, TP53_p.A159P, ELK4_p.S359X, KRAS_p.G12C, RNF43_p.G659X, TP53_p.R248Q, and PIK3CA_p.E545A.

According to the preferred embodiment of the present invention, using the library of aAPC for screening immunogenic peptides according the method 500 from TMGs exclusively activate CD8+ T cells comprising: TCF7L2_p.H198X, SMAD4_p.G30X, MTOR_p.S2215F, ATP1A1_p.G98X, ARID1A_p.S764SX, ASXL1_p.G643X, GNAS_p.R201C, PIK3CA_p.R88Q, PIK3CA_p.E970K, FBXW7_p.S582L, FBXW7_p.R465H, IL7R_p.K119X, EGFR_p.L858R, AKAP9_p.K37X, KRAS_p.A146T, CHD4_p.K73X, TP53_p.E286K, TP53_p.V157F, BARD1_p.K171X, PIK3CA_p.V344G, PIK3CA_p.E542K, AKAP9_p.SE1650-1651SX, KRAS_p.G13D, KRAS_p.G12V, KRAS_p.G12A, KRAS_p.G12D, TP53_p.R282W, GNAS_p.R201H, and BRAF_p.V640E.

According to an exemplary embodiment of the invention, screening results of selected mutations using PBMCs from healthy donors expressing HLA-A1101 that have a characteristic cover by the 47 mutations related to colorectal cancer and lung cancer listed in Table 12 below, and they have been divided into three tiers by NetMHCpan 4.1 tool compared to the graph showing the proportion of Vietnamese patients carrying colorectal cancer and lung cancer.

TABLE 12

Screening results of selected mutations using PBMCs from healthy donors (HD) expressing HLA-A1101

| No. | Peptide ID | Gene name | Mutation | Tier | Number of HD | Number of HD with positive T cell response |
|---|---|---|---|---|---|---|
| 1 | 1 | TCF7L2 | H198X | 3 | 2 | 0 |
| 2 | 3 | ATM | V60X | 3 | 2 | 0 |
| 3 | 30 | SMAD4 | G30X | 3 | 2 | 2 |
| 4 | 33 | MTOR | S2215F | 3 | 2 | 0 |
| 5 | 34 | ATP1A1 | G98X | 3 | 2 | 0 |
| 6 | 36 | ARID1A | S764SX | 3 | 2 | 1 |
| 7 | 38 | ARID1A | G1848X | 3 | 2 | 1 |
| 8 | 39 | ASXL1 | G643X | 3 | 2 | 0 |
| 9 | 40 | GNAS | R201C | 3 | 2 | 1 |
| 10 | 42 | ERG | -446-447X | 3 | 2 | 1 |
| 11 | 44 | DCTN1 | R1173H | 3 | 2 | 1 |
| 12 | 45 | PIK3CA | R88Q | 3 | 2 | 1 |
| 13 | 47 | PIK3CA | R357Q | 3 | 2 | 0 |
| 14 | 51 | PIK3CA | E970K | 3 | 2 | 0 |
| 15 | 53 | FBXW7 | S582L | 3 | 2 | 0 |
| 16 | 54 | FBXW7 | R465H | 3 | 2 | 2 |
| 17 | 58 | IL7R | K119X | 3 | 2 | 1 |
| 18 | 61 | BRAF | D634N | 3 | 2 | 2 |
| 19 | 62 | BRAF | G509V | 3 | 2 | 1 |
| 20 | 63 | EGFR | L858R | 3 | 2 | 0 |
| 21 | 64 | AKAP9 | K37X | 3 | 2 | 0 |
| 22 | 66 | UBR5 | R1331C | 3 | 2 | 0 |
| 23 | 67 | AMER1 | F173X | 3 | 2 | 0 |
| 24 | 7 | NCOR2 | P975X | 3 | 2 | 2 |
| 25 | 8 | KRAS | A146T | 3 | 2 | 0 |
| 26 | 5 | POU2AF1 | A226V | 2 | 3 | 2 |
| 27 | 14 | KRAS | G12S | 2 | 3 | 3 |
| 28 | 15 | CHD4 | K73X | 2 | 3 | 1 |
| 29 | 20 | TP53 | E286K | 2 | 3 | 1 |
| 30 | 28 | TP53 | A159P | 2 | 3 | 1 |
| 31 | 29 | TP53 | V157F | 2 | 3 | 2 |
| 32 | 35 | ELK4 | S359X | 2 | 3 | 0 |
| 33 | 43 | BARD1 | K171X | 2 | 3 | 0 |
| 34 | 46 | PIK3CA | V344G | 2 | 3 | 0 |
| 35 | 48 | PIK3CA | E542K | 2 | 3 | 0 |
| 36 | 65 | AKAP9 | SE1650-1651SX | 2 | 3 | 0 |
| 37 | 9 | KRAS | G13D | 1 | 2 | 2 |
| 38 | 10 | KRAS | G12V | 1 | 2 | 2 |
| 39 | 11 | KRAS | G12A | 1 | 2 | 0 |
| 40 | 12 | KRAS | G12D | 1 | 2 | 0 |
| 41 | 13 | KRAS | G12C | 1 | 2 | 0 |
| 42 | 19 | RNF43 | G659X | 1 | 2 | 2 |
| 43 | 21 | TP53 | R282W | 1 | 2 | 0 |
| 44 | 24 | TP53 | R248Q | 1 | 2 | 0 |
| 45 | 41 | GNAS | R201H | 1 | 2 | 0 |
| 46 | 49 | PIK3CA | E545K | 1 | 2 | 0 |
| 47 | 60 | BRAF | V640E | 1 | 2 | 0 |

Figure 9A:
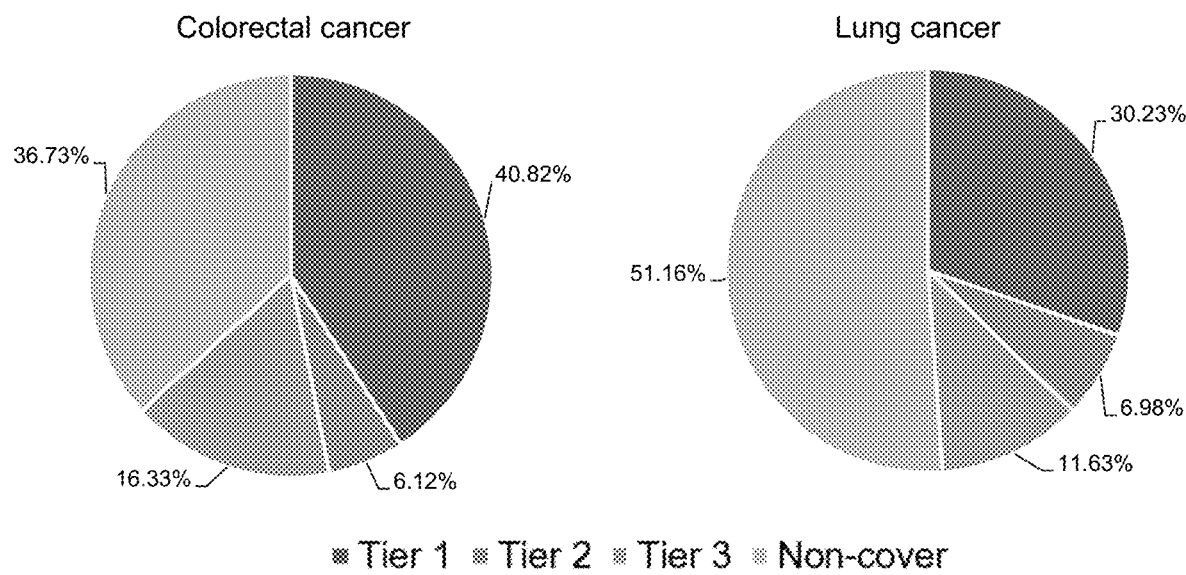
FIG. 9A is a graph illustrated peptides bearing selected mutations covered in colorectal and lung cancer cohort in accordance with an exemplary embodiment of the present invention.
Figure 9B:
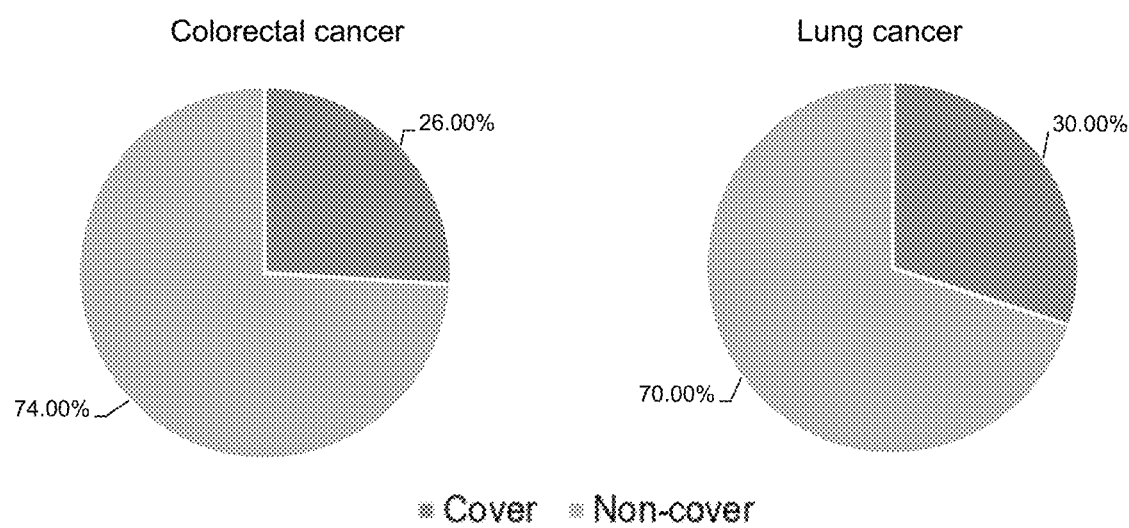
FIG. 9B is a graph illustrated immunogenic neoantigens covered in colorectal (50 patients) and lung cancer (50 patients) cohort in accordance with an exemplary embodiment of the present invention.

As a result the set of peptides bearing selected mutations cover 63.27% (42/67) colorectal and 48.84% (32/67) lung cancer patients in our cohort (referenced by FIG. 9A). The set of validated immunogenic peptides can cover 26% of CRC (13/50) and 30% of lung cancer (15/50) patients in our cohort (referenced by FIG. 9B).

Figure 10:
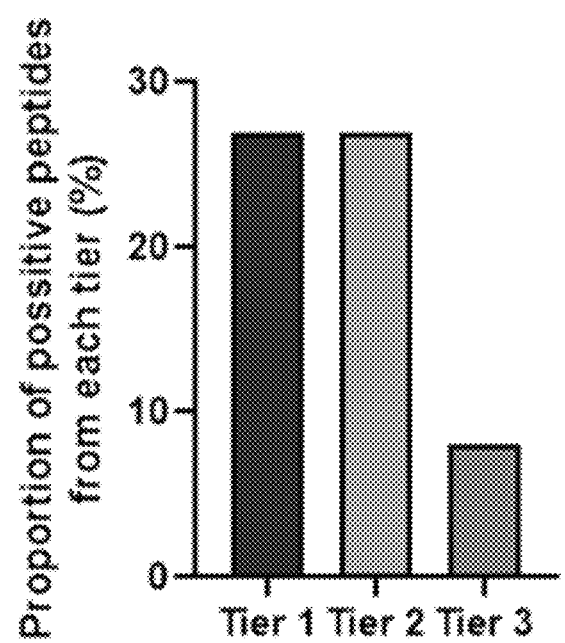
FIG. 10 is a graph illustrated evaluated the proportion of positive peptides in more than two healthy donors in mutations of three tiers in accordance with an exemplary embodiment of the present invention.

According to an exemplary embodiment of the invention, results of compared the IFNγ production by mutant peptides and corresponding wild type peptides as following: fold change of mutant peptide to corresponding wild type peptide is more than two, that mutant peptide is defined as a positive peptide. We evaluated the proportion of positive peptides in more than two healthy donors in mutations of three tiers (referenced by Table 7, and FIG. 10). Tier 1 and 2 peptides show higher proportion of positive peptides than tier 3 peptides (27% for tier 1 and 2 peptides versus 8% for tier 3 peptides). This finding confirms that mutations from tier 1 and 2 display high frequencies and strong binding affinity to common HLA class I of Vietnamese population, demonstrating the effectiveness of mutation classification according to embodiment of the present invention.

Figure 11A:
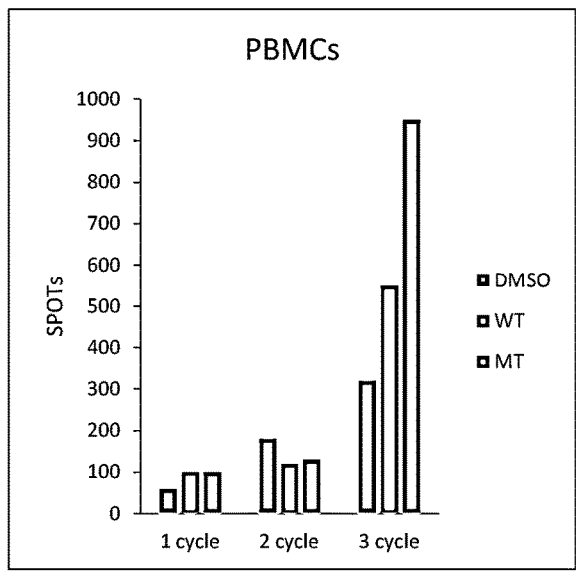
FIG. 11A is a graph illustrated evaluate time consuming for peptide-specific T cell response stimulation by utilization of PBMCs.
Figure 11B:
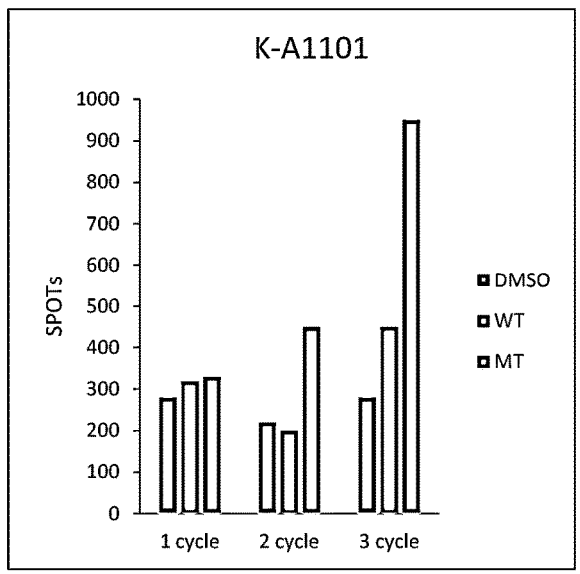
FIG. 11B is a graph illustrated evaluate time consuming for peptide-specific T cell response stimulation by utilization of fixed K562-A1101.
Figure 11C:
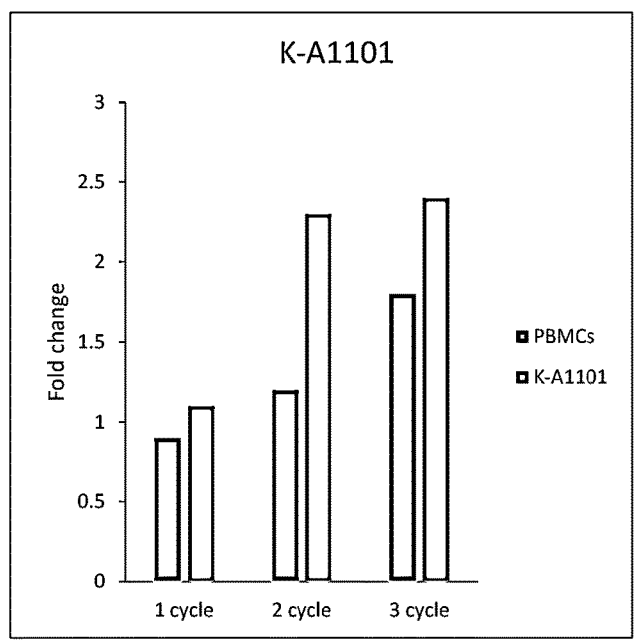
FIG. 11C is a graph illustrated fold change of spot numbers of MT/WT between the utilization of PBMCs for peptide-specific T cell response and the utilization of fixed K562-A1101 for peptide-specific T cell response.

Using mutant peptide (MT (pool)) includes KRAS-G12V peptide and KRAS-G12D peptide, which are containing hotspot mutations in CRC and many type of cancers, to evaluate time consuming for T cell stimulation by PBMCs or aAPC according to the embodiment of the invention, wherein said peptide sequence are published about T cell response to HLA-A1101. Fold changes of IFNγ production by fixed K562-A1101 (referred to as K-A1101 or K-A11) after stimulation with KRAS-G12D peptide and KRAS-G12V peptide are shown in FIG. 11A, and FIG. 11B. As a result, using fixed K562-A1101 could reduce the time-consuming from 14 days (3 cycles) to 6 days (2 cycles) for priming T cell response (referenced by FIG. 11C).

Figure 12:
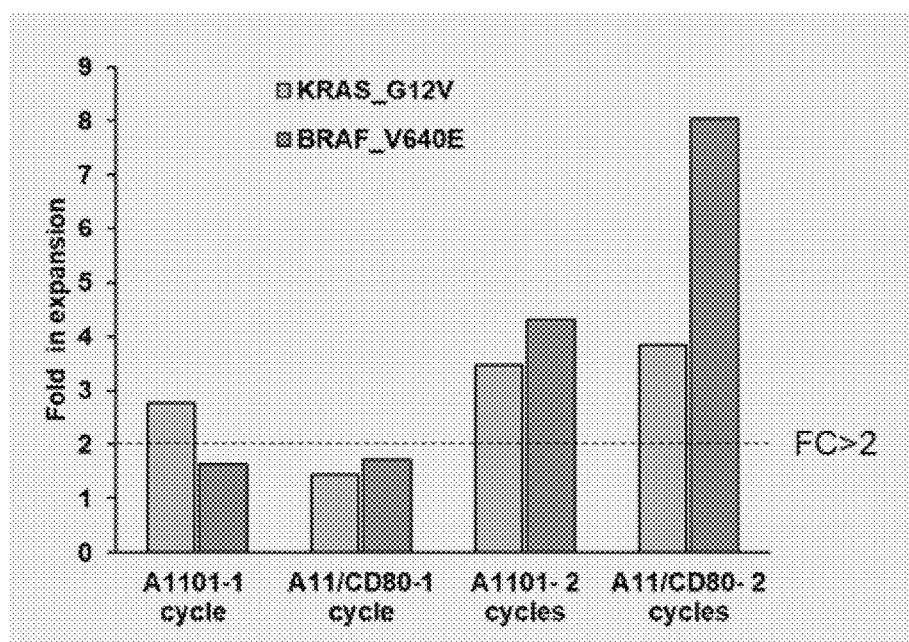
FIG. 12 is a graph illustrated the screening performance of our assay using K562-A1101 or K562-A11/CD80 cells pulsed with peptides (KRAS_G12V or BRAF_V640E)
Figure 13:
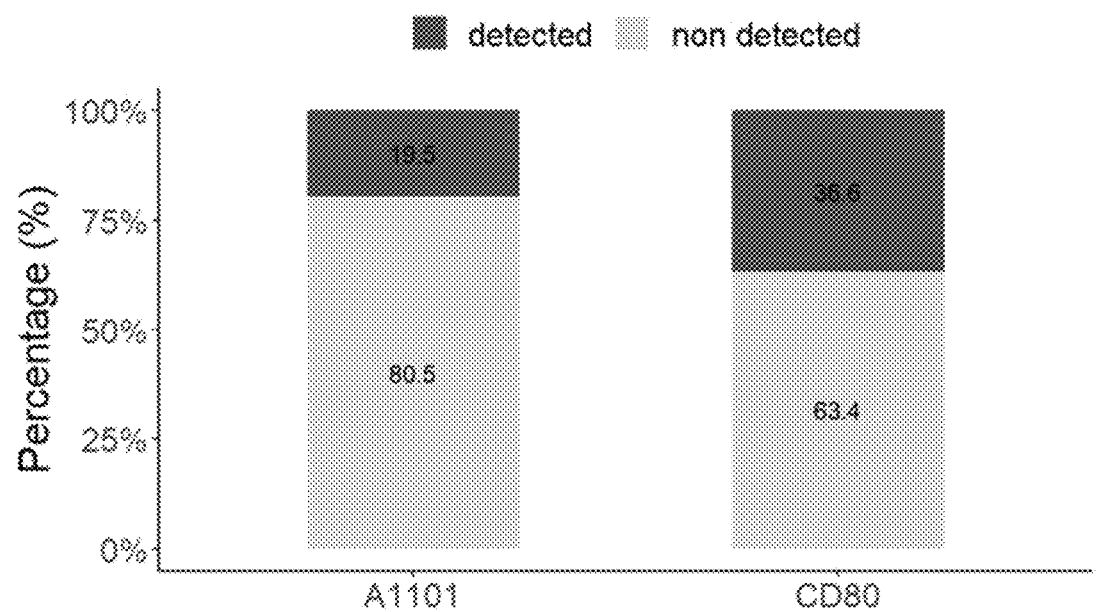
FIG. 13 is a graph illustrated the percentage of immunogenic peptides within 47 mutations when utilizing either A-1101 or A11/CD80, increasing from 19.5% to 36.6%.
Figure 14:
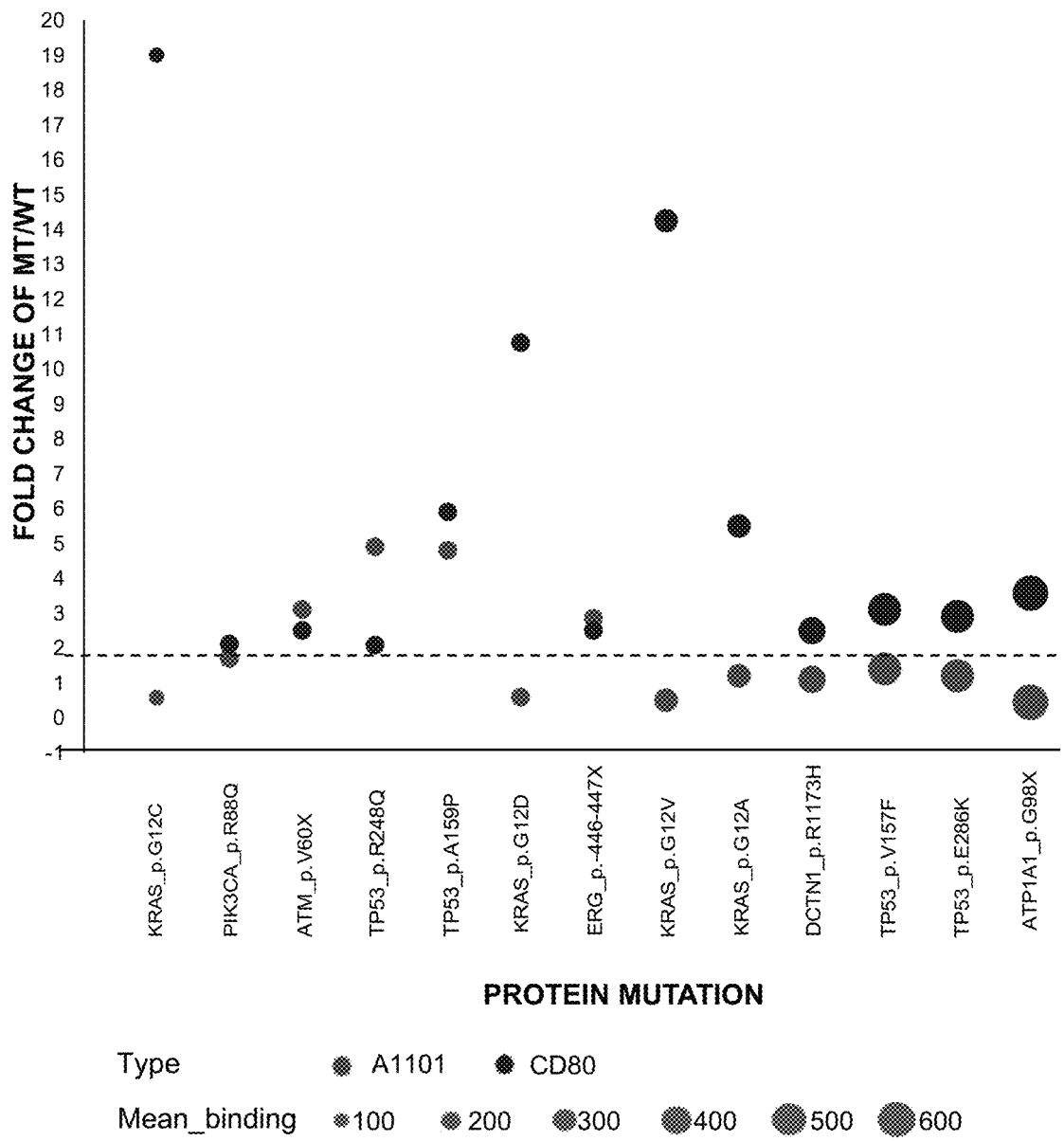
FIG. 14 is a graph illustrated the enhanced stimulation of T-cell responses by CD80 molecules when compared to K-A11/CD80 and K-A1101, which stimulate T-cell responses with peptides exhibiting low binding affinity.
Figure 15:
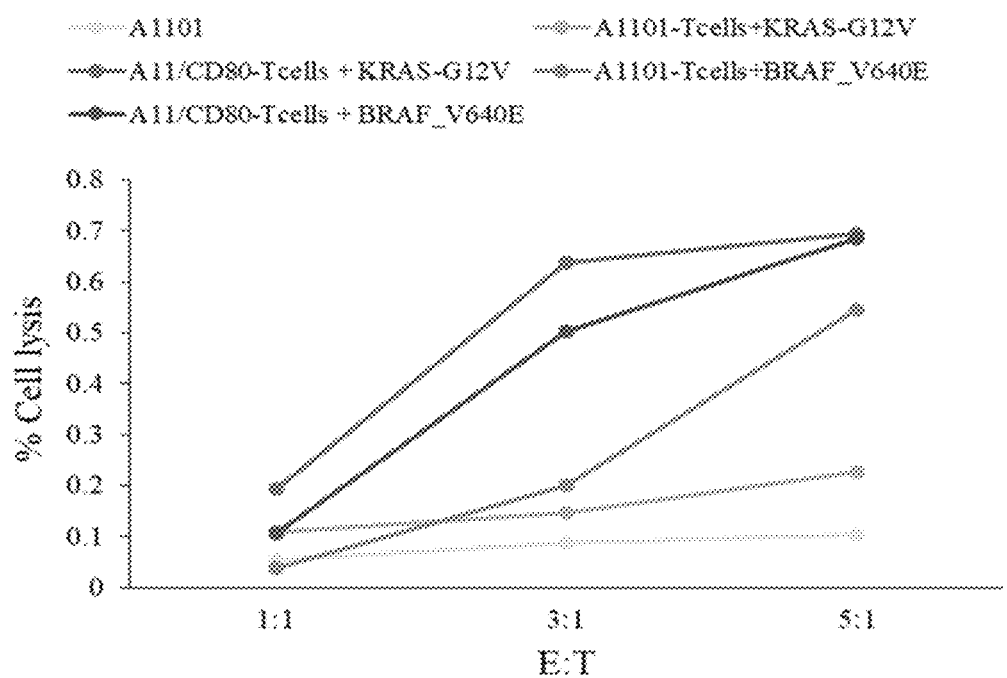
FIG. 15 is a graph illustrated the stronger cytotoxic activity of antigen-specific T cells from K562-A11/CD80 compared to that from K562-A1101 in accordance with an exemplary embodiment of the present invention.

Referring to survey experiment of aAPC transfected with co-stimulatory molecule can elicit strong and long-lasting antigen-specific T responses to low immunogenicity cancer antigens according method following as: generating library of aAPC co-express MHC class I with CD80. Then, K-A1101/CD80 (or K-A11/CD80) cells were used to evaluate the effect of CD80 on T cell response. Mutant peptides are used for evaluation including KRAS_G12V, and BRAF_V640E. To demonstrate the superior performance of K-A11/80, performing the comparison its ability to present a weak immunogenic neopeptide BRAF_V640E and activate T cell responses with K-A11. A strong immunogenic KRAS_G12V neopeptides were used as a control. As results K-A11/CD80 or K562-A1101 were cocultured with T cells and stimulated with different peptides. T cell numbers were counted after 3 days (1 cycle) and 6 days (2 cycles) coculture. Expanded T cell after 6 days coculture (referenced by FIG. 12). The result of expansion is dependent on the peptides. However, K-A11/CD80 could expand T cell more than K-A1101. Then, evaluated if K-A11/CD80 could be used as immunogenicity screening system or not by validated the IFNγ production by ELISpot based on the percentage of immunogenic peptides within 47 mutations when utilizing either A-1101 or A11/CD80 (increasing from 19.5% to 36.6%, that referenced by FIG. 13). As a result, K-A11/CD80 could stimulate T cell response to KRAS-G12V peptide after 3 days priming compared to K562-A1101 with 6 days priming. K-A11/CD80 might shorten the length of screening time compared to K562-A1101 or PBMC. In addition, the results also show the ability to screen neopeptides with low affinity (>0.5%), specifically K-A11/CD80 can stimulate T cell response to weak immunogenic neopeptide BRAF_V640E compared to K562-A1101 cannot stimulate T cell response to weak immunogenic neopeptide BRAF_V640E via log 2 fold change of ELISpot (referenced by FIG. 14). Moreover, the results also show the cytotoxicity of antigen-specific T cells from K-A11/CD80 was stronger than K562-A1101 (referenced by FIG. 15). In order to test the antigen-dependent cytolytic activity, antigen-specific lysis was measured after 12 hours exposure to peptide pulsed or unpulsed K562-A1101 at 5:1, 3:1, and 1:1 E:T ratios. T cell lines generated with peptide pulsed, fixed K562-A1101 and K-A11/CD80 demonstrated clear HLA-A*1101 restricted neopeptide-specific cytotoxicity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:
1. A method for neoantigen screening from recurrent cancer mutations comprising steps performed in the following specific order:
- (A) STEP 1: selecting recurrent cancer mutations by performing steps (i) to (iii):
  - (i) Collecting colorectal cancer (CRC) and lung cancer data, then the data are processed to obtain a set of selected mutations including single nucleotide variations (SNVs), and insertions/deletions variants (Indels);
  - (ii) classifying the set of selected mutations to obtain 67 identified mutations, wherein the 67 identified mutations are divided into three tiers including a first tier, a second tier, and a third tier; wherein the first tier includes the following identified mutations KRAS_p.G13D, KRAS_p.G12V, KRAS_p.G12A, KRAS_p.G12D, KRAS_p.G12C, CDX2_p.V306X, RNF43_p.G659X, TP53_p.R282W, TP53_p.R273H, TP53_p.R248Q, TP53_p.R175H, GNAS_p.R201H, PIK3CA_p.E545K, and BRAF_p.V640E;
  wherein the second tier includes the following identified mutations TCF7L2_p.R471C, ATM_p.A2301X, POU2AF1_p.A226V, KRAS_p.G12S, CHD4_p.K73X, TP53_p.E286K, TP53_p.Y220C, TP53_p.C176F, TP53_p.A 159P, TP53_p.V157F, CIC_p.T1740M, ELK4_p.S359X, ARID1A_p.K1071 X, BARD1_p.K171 X, PIK3CA_p.V344G, PIK3CA_p.E542K, and AKAP9_p.SE1650-1651SX; and
  wherein the third tier includes the following identified mutations TCF7L2_p.H198X, ATM_p.V60X, BCL9L_p.Q452X, NCOR2_p.P975X, KRAS_p.A146T, BRCA2_p.Q1782X, COK12_p.R663C, TP53_p.R273C, SMAO4_p.G30X, SMAO4_p.R361H, MTOR_p.S2215F, ATP1A1_p.G98X, ARID1A_p.S764SX, ARID1A_p.G1848X, ASXL 1_p.G643X, GNAS_p.R201 C, ERG_p.-446-447X, AMER1_p.F173X, DCTN1_p.R1173H, PIK3CA_p.R88Q, PIK3CA_p.R357Q, PIK3CA_p.E545A, PIK3CA_p.E970K, FAT4_p.L3V, FBXW7_p.S582L, FBXW7_p.R465H, PDGFRA_p.R151 H, APC_p.M1413X, APC_p.KR1462-1463X, IL7R_p.K119X, IL6ST_p.K529X, BRAF p.O634N, BRAF p.G509V, EGFR_p.L858R, AKAP9_p.K37X, and UBR5_p.R1331 C; and
  - (iii) Designing and synthesizing the 67 identified mutations in the form of tandem minigenes to obtain a collection of tandem minigene (TMG) constructs (referred to as the TMGs) by concatenating the 67 identified mutations divided into three tiers at Step 1(ii), in which each TMG contains 10 identified mutations belong to the same tier;
- (B) STEP 2: Generating a library of artificial antigen presenting cells (aAPC) co-expressing HLA types and CD80 molecules (referred to as the library of aAPC) by performing the steps:
  - (i') collecting HLA type data from a public database and ranking HLA types based on their frequencies in the population of 7 Asian countries, resulting in a list of 13 most frequent HLA class I types in the populations of the 7 Asian countries, and a list of 04 most frequent HLA class II types in the populations of the 7 Asian countries is obtained; and
  in which the 7 Asian countries consist of China, Indonesia, Japan, Malaysia, Vietnam, South Korea, and Thailand;
  wherein the list of 13 most frequent HLA class I types in the populations of the 7 Asian countries comprises three main group alleles: HLA-A, HLA-8, and HLA-C' all determined as allele groups popular to the population of the 7 Asian countries including: A*1101, A*0201, A*0203, A*2402, A*0301, A*3303, 8*1502, 8*4001, 8*4601, C*0102, C*0702, C*0B01, and C*0304;
  wherein the list of 04 most frequent HLA class II types in the populations of the 7 Asian countries comprises two main group alleles: HLA-DR81, and HLA-DQ81; all determined as allele groups popular to the population of the 7 Asian countries including: DR81*0901, DR81*1202, DQ81*0303, and DQ81*0301; and
  - (ii') generating the library of aAPC including a library of aAPC by genetically engineering K562 cells to co-express selected HLA class I types at step (i') and the CD80 molecules; and a library of aAPC by genetically engineering K562 cells to co-express selected HLA class II types at step (i') and the CD80 molecules; and
- (C) STEP 3: using the library of aAPC at step 2(B) for rapid and comprehensive screening for selecting of immunogenic peptides (neoantigens) from the TMGs at step 1(A) that activate T cells via immunological assays.

2. The method of claim 1, wherein generating the library of aAPC by genetically engineering K562 cells to co-express HLA class I types and CD80 molecules, comprising the following steps:
- (a') generating a medium containing lentiviral vector carrying CD80 molecules by performing the steps in the following order:
  seeding 8×10$^6$ 293T cells into 10 cm$^2$ plate for 24 hours; then transfecting in a medium supplemented with 10% FBS, 100 units/ml penicillin, and 100 µg/ml streptomycin at 37° C. in a humidified 5% CO$_2$ incubator; co-transfecting third generation lentivirus helper plasmids and pLT-CD80 transfer plasmid into 293T cell line to produce lentiviral vector particles; wherein the third generation lentivirus helper plasmids includes a RSV packaging plasmid, MDIg regulatory plasmid, and MD2G envelope plasmid;
  replacing the medium with fresh medium at 6 hours post-transfection; and collecting the medium containing lentiviral vector in conical tubes at 72 hours and storing;
- (b') transducing stably the K562 cells expressing HLA class I types with the lentiviral vector carrying CD80 molecules and adding 8 µg/mL of polybrene (in a 24 well-plate, wherein each plate is centrifuged at 1000×g for 30 mins; and
- (c') sorting single cell clones co-expressing the HLA class I types and CD80 molecules and expanding to establish cell lines.

3. The method of claim 1, wherein generating the library of aAPC by genetically engineering K562 cells to co-express HLA class II types and the CD80 molecules, comprising the following steps:
- (a") generating a medium containing lentiviral vector carrying CD80 molecule by performing the steps in the following order:

seeding 8×10⁶ 293T cells into 10 cm² plate for 24 hours; then transfecting in a medium supplemented with 10% FBS, 100 units/ml penicillin, and 100 µg/ml streptomycin at 37° C. in a humidified 5% CO$_2$ incubator;

co-transfecting third generation lentivirus helper plasmids and pLT-CD80 transfer plasmid into a 293T cell line to produce lentiviral vector particles; wherein the third generation lentivirus helper plasmids include a RSV packaging plasmid, MDIg regulatory plasmid, and MD2G envelope plasmid;

replacing the medium with fresh medium at 6 hours post-transfection; and collecting the medium containing lentiviral vector in conical tubes at 72 hours and storing;

(b") transducing stably the K562 cells expressing HLA class II types with the lentiviral vector carrying CD80 molecules and adding 8 µg/mL of polybrene in a 24 well-plate, wherein each plate is centrifuged at 1000×g for 30 mins; and (c") sorting single cell clones co-expressing the HLA class II types and CD80 molecules and expanding to establish cell lines.

4. The method of claim 1, wherein using the library of aAPC at step 2(B) for screening and selecting immunogenic peptides (neoantigens) from the TMGs at step 1(A) to activate T cells within 11 days, comprising the following steps:

(A") generating a TMG mRNA-transfected aAPC at day 1, comprising the following steps;

(a2) culturing T cells isolated from PBMCs of healthy donor carrying appropriated HLA class I or HLA class II type in media supplemented with 10% FBS, and 10 ng/ml of ll-21 and T cells are enriched by CD3 marker;

(b2) culturing corresponding K562 aAPC cells expressing HLA class I or HLA class II in RPMI1640 media supplemented with 10% FBS, and 1% PS; and (c2) synthesizing TMG mRNAs and transfecting into the K562 aAPC cells, and culturing for overnight, resulting in the TMG mRNA-transfected aAPC;

(B") generating antigen-specific T cells from day 2 to day 5, comprising the following steps:

Fixing the TMG m RNA-transfected aAPC with 0.1% formaldehyde for ten minutes at room temperature (RT); and Washing one time with PBS and one time with culture media to remove formaldehyde and co-culturing with T cells in T cell media supplemented with 10 ng/ml of IL-7, 10 ng/ml of IL-21, and 10 ng/ml of IL-15 at the ratio of 2:1 (T cells: fixed aAPC cells) for 3 days;

wherein T cells isolated from PBMCs of healthy donor carrying appropriated HLA class I or HLA class II type are cultured in AIM-V media supplemented with 10% FBS, and 10 ng/ml of IL-21; and T cells are enriched by a CD3 marker;

(C") Restimulating the antigen-specific T cells via the TMG mRNA-transfected aAPC at step (B") in T cell media without interleukin stimulation overnight and co-culturing with T cells in T cell media supplemented with 10 ng/ml of IL-7, 10 ng/ml of IL-21, and 10 ng/mL of IL-15 for 3 days;

(D") Restimulating the antigen-specific T cells with the TMG mRNA-transfected aAPC and coculturing in media without cytokines at day 9;

(E") Counting 10⁵ T cells and seeding into the plate for interferon-γ quantification at day 10; and (F") Quantifying of interferon-γ newly isolated peripheral blood mononuclear cells (PBMCs), resulting in obtaining the immunogenic peptides (neoantigens) at day 11.

5. The method of claim 4, wherein using the library of aAPC at step 2(B) for screening immunogenic peptides from the TMGs at step (A) carrying identified mutations activate both CD4+ T cells and CD8+ T cells or exclusively activate CD8+ T cells.

6. The method of claim 5, wherein the TMGs at step 1(A) carrying identified mutations activate both CD4+ T cells and CD8+ T cells comprising: ATM_p.V60X, ARID1A_p.G1848X, ERG_p.-446-447X, DCTN1_p.R1173H, PIK3CA_p.R357Q, BRAF_p.D634N, BRAF_p.G509V, UBR5_p.R1331C, AMER1_p.F173X, NCOR2_p.P975X, POU2AF1_p.A226V, KRAS_p.G12S, TP53_p.A159P, ELK4_p.S359X, KRAS_p.G12C, RNF43_p.G659X, TP53_p.R248Q, and PIK3CA_p.E545A.

7. The method of claim 5, wherein the TMGs at step 1(A) carrying identified mutations exclusively activate CD8+ T cells comprising: TCF7L2_p.H198X, SMAD4_p.G30X, MTOR_p.S2215F, ATP1A1_p.G98X, ARID1A_p.S764SX, ASXL1_p.G643X, GNAS_p.R201C, PIK3CA_p.R88Q, PIK3CA_p.E970K, FBXW7p.S582L, FBXW7_p.R465H, IL7R_p.K119X, EGFR_p.L858R, AKAP9_p.K37X, KRAS_p.A146T, CHD4_p.K73X, TP53_p.E286K, TP53_p.V157F, BARD1_p.K171X, PIK3CA_p.V344G, PIK3CA_p.E542K, AKAP9_p.SE1650-1651SX, KRAS_p.G13D, KRAS_p.G12V, KRAS_p.G12A, KRAS_p.G12D, TP53_p.R282W, GNAS_p.R201H, and BRAF_p.V640E.

* * * * *